(12) United States Patent
Bradbury

(10) Patent No.: US 8,227,242 B2
(45) Date of Patent: Jul. 24, 2012

(54) PLASMIDS AND PACKAGING CELL LINES FOR USE IN PHAGE DISPLAY

(75) Inventor: Andrew M. Bradbury, Santa Fe, NM (US)

(73) Assignee: Los Alamos National Security, LLC, Los Alamos, NM (US)

(*) Notice: Subject to any disclaimer, the term of this patent is extended or adjusted under 35 U.S.C. 154(b) by 258 days.

(21) Appl. No.: 11/636,023

(22) Filed: Dec. 7, 2006

(65) Prior Publication Data
US 2007/0128728 A1    Jun. 7, 2007

Related U.S. Application Data

(60) Provisional application No. 60/748,504, filed on Dec. 7, 2005.

(51) Int. Cl.
*C12N 15/63* (2006.01)
*C12N 1/21* (2006.01)
(52) U.S. Cl. .................................. 435/320.1; 435/252.3
(58) Field of Classification Search .................... None
See application file for complete search history.

(56) References Cited

U.S. PATENT DOCUMENTS

| 5,223,409 A * | 6/1993 | Ladner et al. ................. 506/1 |
| 6,080,569 A * | 6/2000 | Graham et al. ............ 435/235.1 |
| 2003/0104604 A1 | 6/2003 | Yang et al. |

OTHER PUBLICATIONS

Sidhu, S. Engineering M13 for phage display. Biomol Eng. Sep. 2001;18(2):57-63.*
Endemann et al. The adsorption protein of phage IKe. Localization by deletion mutagenesis of domains involved in infectivity. Mol Microbiol. Feb. 1992;6(4):471-8.*
Guilfoyle et al. A direct selection strategy for shotgun cloning and sequencing in the bacteriophage M13. Nucleic Acids Res. Jan. 11, 1994;22(1):100-7.*
Rakonjac and Jovanovic, 1997, Gene 198, 99-103.
Duenas, 1995, FEMS Microbiol. Lett. 125: 317-321.
Soltes et al., 2003, J. Immunol. Methods 274:233-244.
Rondot et al, 2001, Nat. Biotechnol. 19: 75-78.
Baek et al, 2002, Nucleic Acids Res. 30: e18.
Kramer et al., 2003, Nucleic Acids Res. 31: e59.
Jestin et al, 2001, Res Microbiol. 152: 187-191.
Sblattero and Bradbury, 2000, Nat. Biotechnol. 18: 75-80.
Sidhu et al, 2000, Methods Enzymol. 328: 333-363.
Bradbury et al., 2003, Trends Biotechnol. 21: 275-281.
Bradbury et al., 2003, Trends Biotechnol. 21: 312-317.
Scholle, M. D. et al., "Efficient Construction of a Large Collection of Phage-Displayed Combinatorial Peptide Libraries," Combinatorial Chemistry & High Throughput Screening, vol. 8 (Sep. 2005) pp. 545-551.
Guilfoyle, R. A. et al., "A Direct Selection Strategy for Shotgun Cloning and Sequencing in the Bacteriophage M13," Nucleic Acids Research, vol. 22 (Oct. 1994) pp. 100-107.
Chasteen, L. et al., "Eliminating Helper Phage from Phage Display," Nucleic Acids Research, vol. 34 (Nov. 2006) pp. e145.
WO/2002/103012 A1, Published Dec. 27, 2002.
Russell, M. et al., "Genetic Analysis of the Filamentous Bacteriophage Packaging Signal and of the Proteins that Interact with it," Journal of Virology, vol. 63 (Aug. 1989) pp. 3284-3295.
Chasteen et al., "Eliminating helper phage from phage display," *Nucleic Acids Res*, vol. 31:e145, 2006.
Yanisch-Perron et al., "Improved M13 Phage Cloning Vectors and Host Strains: Nucleotide Sequences of the M13mp18 and pUC19 Vectors," *Gene*, vol. 33:103-119, 1985.

* cited by examiner

*Primary Examiner* — Michele K Joike
(74) *Attorney, Agent, or Firm* — Klarquist Sparkman, LLP

(57) ABSTRACT

The invention relates to a novel phagemid display system for packaging phagemid DNA into phagemid particles which completely avoids the use of helper phage. The system of the invention incorporates the use of bacterial packaging cell lines which have been transformed with helper plasmids containing all required phage proteins but not the packaging signals. The absence of packaging signals in these helper plasmids prevents their DNA from being packaged in the bacterial cell, which provides a number of significant advantages over the use of both standard and modified helper phage. Packaged phagemids expressing a protein or peptide of interest, in fusion with a phage coat protein such as g3p, are generated simply by transfecting phagemid into the packaging cell line.

25 Claims, 8 Drawing Sheets

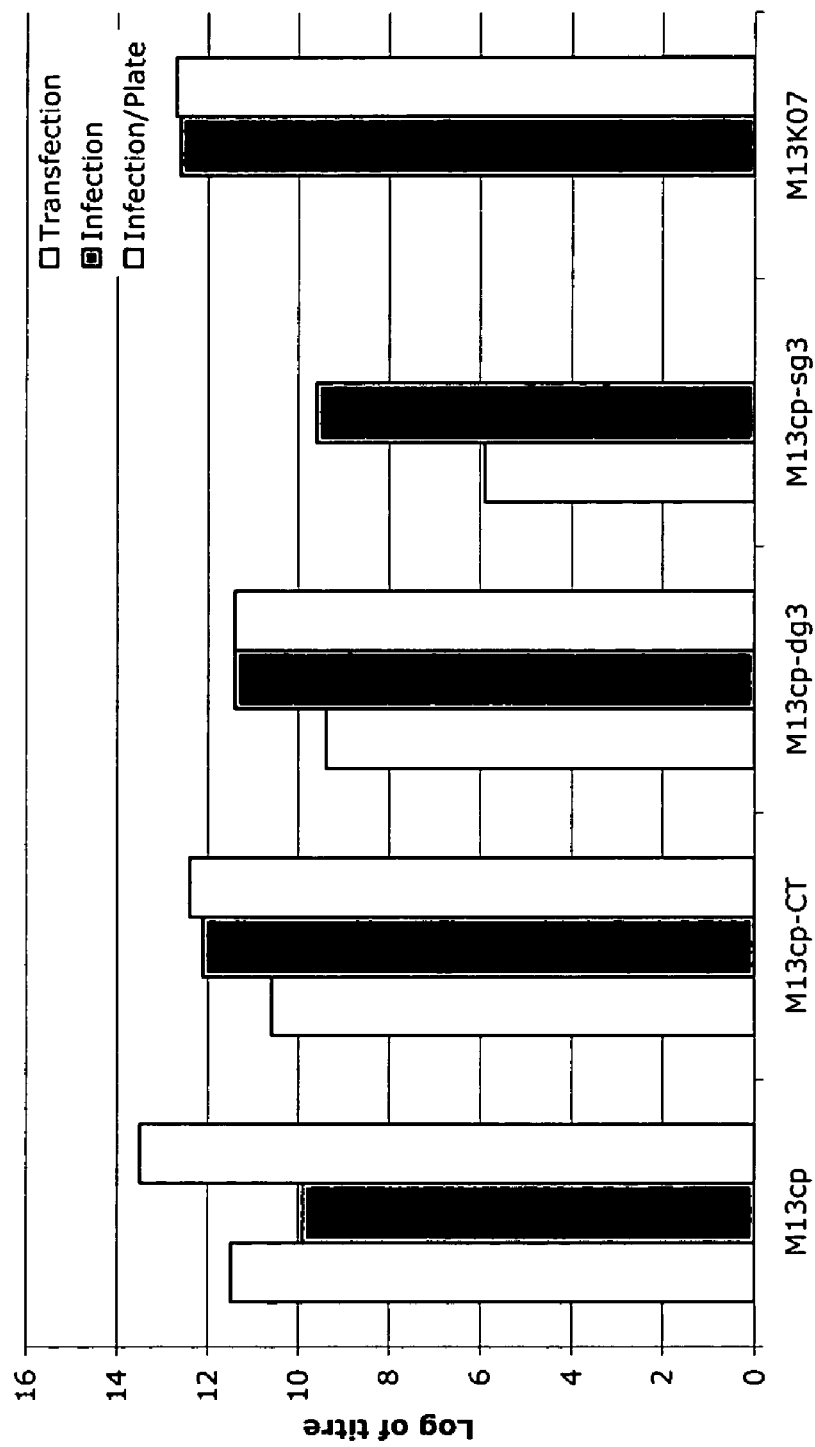

PLASMIDS AND PACKAGING CELL LINES FOR USE IN PHAGE DISPLAY

RELATED APPLICATIONS

This patent application claims the benefit of the filing date of U.S. Provisional patent application No. 60/748,504 filed Dec. 7, 2005.

STATEMENT AS TO RIGHTS TO INVENTIONS MADE UNDER FEDERALLY SPONSORED RESEARCH OR DEVELOPMENT

This invention was made with government support under Contract No. W-7405-ENG-36 awarded by the United States Department of Energy to The Regents of The University of California. The government has certain rights in this invention.

BACKGROUND OF THE INVENTION

Phage display technology, i.e., the use of filamentous phage to display recombinant proteins and peptides, is well known and used for selecting proteins and peptides with desired functions or improved characteristics from complex libraries. Phage display is widely used for the isolation of human antibodies through clonal selection of antibody fragments in prokaryotic host systems. Filamentous phage from the Ff group, including M13, f1 and fd phage, are commonly used. Vectors capable of directing the generation of recombinant phage and phagemid expressing fusions of viral coat proteins with proteins of interest in $E.\ coli$ have been developed and are widely available. There are two broad categories of vectors used for phage display: phage and phagemid.

When proteins are displayed on phage, the gene encoding the recombinant display protein is included in the phage genome. As a result, all phage particles display the recombinant protein and contain only the recombinant phage genome. In the case of phagemid, the recombinant protein is encoded as a fusion with the g3p on a plasmid (phagemid) which also contains the filamentous phage packaging signal. Bacteria carrying such phagemids make large amounts of the recombinant display protein, but are unable to make phage unless the bacteria carrying the phagemid also contain helper phage, which supply all the other proteins required to make functional phage.

Helper phages[1, 2] are essentially normal Ff phages with a number of modifications: their packaging signal is severely disabled, they contain an additional origin of replication, and they usually carry antibiotic resistance genes. The disabled packaging signal does not prevent the helper phage from making phage particles when alone in a bacterium, but in the presence of a phagemid, which has an optimal packaging signal, the phagemid should be packaged in preference to the helper phage. As a result, phagemid preparations are both phenotypically and genotypically heterogeneous (FIG. 1). Accordingly, the displayed protein may be either wild type (derived from the helper phage) or recombinant (derived from the phagemid), and the packaged genome may be either phage or phagemid (see FIG. 1).

The different antibiotic resistance genes carried by phage and phagemid allow one to select for bacteria that contain both the phagemid and the helper phage. While the disabled packaging signal in helper phage should significantly reduce the presence of helper phage in any phagemid preparation, helper phage can sometimes be present at levels equal to, or exceeding, phagemid levels. This can significantly compromise subsequent selections.

Phagemid and phage libraries differ in a number of practical ways, and in general, the use of phagemids provides several advantages. At the DNA level (preparing DNA, cloning, transfection efficiency), phagemids are easier to work with, and as a result, phagemid libraries can be made far larger than phage libraries. It is also easier to produce soluble proteins in phagemids when an amber stop codon is inserted between the displayed protein and g3p[3]. Although soluble protein could theoretically be made in phage display libraries using a similar genetic arrangement, the low copy number of the vector and the weakness of the g3p promoter and ribosome binding site, results in levels of soluble protein which are too low for most practical purposes, requiring recloning into expression vectors[4]. Another advantage of phagemids concerns the relative resistance to deletions of extraneous genetic material. Filamentous phage vectors, in general, have a tendency to delete unneeded DNA, as a result of the selective growth advantage a smaller phage has over a larger one. Phagemids suffer far less from this disadvantage and as a result are more stable.

However, phage libraries have considerable operational advantages. To amplify phage libraries it is sufficient to grow bacteria, and phage are produced. There is no need to add helper phage, and subsequent antibiotics, at specific optical densities. This makes phage far easier to use in selections, and also makes automation far more straightforward. Furthermore, the genetic and phenotypic homogeneity of phage libraries eliminate the possibility of helper phage overgrowth. As each phage particle in a phage library displays up to five copies of the displayed protein (using a g3p display system), and only 1-10% of phage particles in a phagemid library display a single copy of the displayed protein[5], antibodies selected from phage libraries tend to be more diverse, but have lower average affinities, a result of the avidity effects caused by the display of multiple proteins per phage particle[4].

Phagemid display, by virtue of the display of single proteins, results in the selection of fewer unique binders, which tend to have higher affinities[4]. For similar reasons, affinity maturation[6-9] can only be carried out with phagemid vectors.

Recently, a number of groups[2, 10-14] have attempted to combine some of the advantages of phage and phagemids by creating helper phages deleted or mutated in gene 3. Initial experiments involved the creation of g3p deleted helper phage, packaged in bacterial strains expressing gene 3 in trans. These allowed higher display levels, but suffered from the problem that when p3 was derived from plasmids, but not the $E.\ coli$ chromosome[12], such plasmids could also be packaged, albeit at low levels[2], and that helper phage titers tend to be very low. More recently, conditional g3p deletions have been created by the introduction of suppressible stop codons in g3[11, 13], allowing production of helper phage in suppressor strains, and the packaging of phagemids in non-suppressor strains, where the helper phage is unable to make its own g3p. An alternative method[14] involves a helper phage which has part of g3 deleted (CT helper phage). This deleted p3 can incorporate into phagemid particles, but because it lacks the N1/2 domains is unable to participate in infection, with the net result that phagemid not displaying the recombinant g3p fusion protein are unable to propagate. In practice, although not in theory, this is similar to a modified helper phage system[15] in which a trypsin site is introduced within the helper phage g3p. When trypsin is used for elution, all phagemid particles containing only helper phage g3p are inactivated and prevented from infecting and subsequent propagation. Both systems result in a lower background during selection. These different helper phage systems are compared in Table 1.

Although it is difficult to compare the different systems, those containing suppressible stop codons in g3[11, 13] appear to be most effective, given that they produce helper phage, and phagemid, titers, as high as, or almost as high as, standard helper phage. Although these systems may overcome some of the disadvantages of helper phage, they do not avoid one of the main problems associated with the use of helper phage: the need to make helper phage and add it to growing bacterial cultures at relatively restricted phases of the growth cycle.

SUMMARY OF THE INVENTION

The invention provides a phagemid display system which eliminates the need for helper phage. The system of the invention utilizes bacterial packaging cell lines containing helper plasmids derived from filamentous phage, such as M13, and enables simplified generation of pure phagemid particle preparations without the phage contamination typical of phage display systems. The concept of the invention is briefly illustrated in FIG. 1.

In one aspect, the invention provides helper plasmids useful in the generation of bacterial cells capable of packaging recombinant phagemid when transfected with phagemid DNA, comprising a polynucleotide encoding a filamentous phage genome or derivative thereof and a heterologous origin of replication (for example, a replication origin belonging to a compatibility group different from the origin used in the phagemid DNA), in which the phage packaging signal has been deleted or otherwise functionally inactivated. In some embodiments, a selectable marker such as an antibiotic resistance marker is included. The invention is exemplified by helper plasmids derived from M13mp19, in which the chloramphenicol resistance gene replaces the lac Z gene and polylinker, and the M13 origin is replaced by the p15a origin. These helper plasmids (see Examples, infra) encode M13 gene 3 coat protein (g3p) variants, i.e., either full length g3p, truncated g3p, or deleted or functionally disabled g3p. The results generated with these helper plasmids show that they are as efficient at packaging phagemid particles as are helper phage, but eliminate helper phage contamination, resulting in genetically pure phagemid preparations (see Example 1, infra).

In another aspect, the invention provides bacterial packaging cell lines for use in phagemid display. In one embodiment, the bacterial packaging cell lines comprise *E. coli* cells. The bacterial packaging cell lines of the invention are characterized by the presence of a helper plasmid of the invention therein, i.e., a plasmid engineered to contain a modified phage genome, wherein the phage packaging signal has been deleted of otherwise functionally disabled. In some embodiments, the replication origin is replaced by a replication origin belonging to a compatibility group different from the origin used in the phagemid DNA. In some embodiments, a selectable marker, such as an antibiotic resistance gene, is also included. The helper plasmid, and thus bacterial cells transformed with the helper plasmid, supplies all required phage proteins but not the packaging signals. The absence of packaging signals in these helper plasmids prevents their DNA from being packaged, which provides a number of significant advantages over the use of both standard[1, 2] and modified helper phages[2, 10-14]. Packaged phagemids expressing a protein or peptide of interest, in fusion with a phage coat protein such as g3p, are generated simply by transfecting phagemid into the packaging cell line.

In a related aspect, the invention provides methods for generating packaged phage particles, comprising introducing a phagemid (via transfection, infection, and the like) into a bacterial cell containing a helper plasmid of the invention. In one embodiment, a method for generating pure recombinant phagemid particles displaying a heterologous polypeptide in bacteria is provided, comprising introducing phagemid DNA encoding the heterologous polypeptide, in fusion with a filamentous phage coat protein (e.g., g3p, g6p, g7p, g8p, g9p), into bacteria containing a helper plasmid of the invention, wherein the helper plasmid encodes a selectable marker (i.e., antibiotic resistance gene) and all required phage proteins (in combination with phage proteins provided in trans, i.e., via a phagemid), and a heterologous origin of replication (including, without limitation, p15a, ColE1, pSC101, pMB1, F, R6K and RK2), but does not encode a packaging signal. Phagemid DNA may be introduced into bacteria by transfection or infection protocols, as is generally known. In a further related aspect, the invention provides a novel method for displaying heterologous polypeptides on a phagemid particle.

In one embodiment, helper plasmid encoding full length gene 3 is used to generate pure phagemid preparations in which the displayed protein is displayed monovalently. The use of helper plasmids with full length g3p results in high affinity display of library proteins. In another embodiment, helper plasmid encoding a truncated gene 3 is used to generate pure phagemid preparations in which the displayed protein is displayed multivalently. The use of helper plasmids with truncated g3p results in high diversity display. In yet another embodiment, helper plasmids in which gene 3 is deleted or rendered non-functional (e.g., by introducing stop codons), are used to generate pure phagemid preparations characterized by multimeric display. The variable display characteristics of the exemplary set of M13 helper plasmids of the invention (see Examples, infra) enable selections based on either monovalent/high affinity display or multivalent/high diversity display, by choosing from alternative helper plasmids (i.e., M13cp vs. M13cp-CT), and thus provides a convenient way to conduct variable selections from the same library.

BRIEF DESCRIPTION OF THE DRAWINGS

FIG. 2A: titer of pDAN5-D1.3 phagemid produced by bacteria under three different conditions: a) transfection into bacteria containing each helper plasmid, plate on ampicillin chloramphenicol plates, pick a single colony and grow overnight; b) infect pDAN5-D1.3 phagemids into bacteria and grow overnight directly in liquid media; and c) infect, plate on ampicillin chloramphenicol plates, pick a single colony and grow overnight.

DETAILED DESCRIPTION OF THE INVENTION

Definitions

Figure 1:
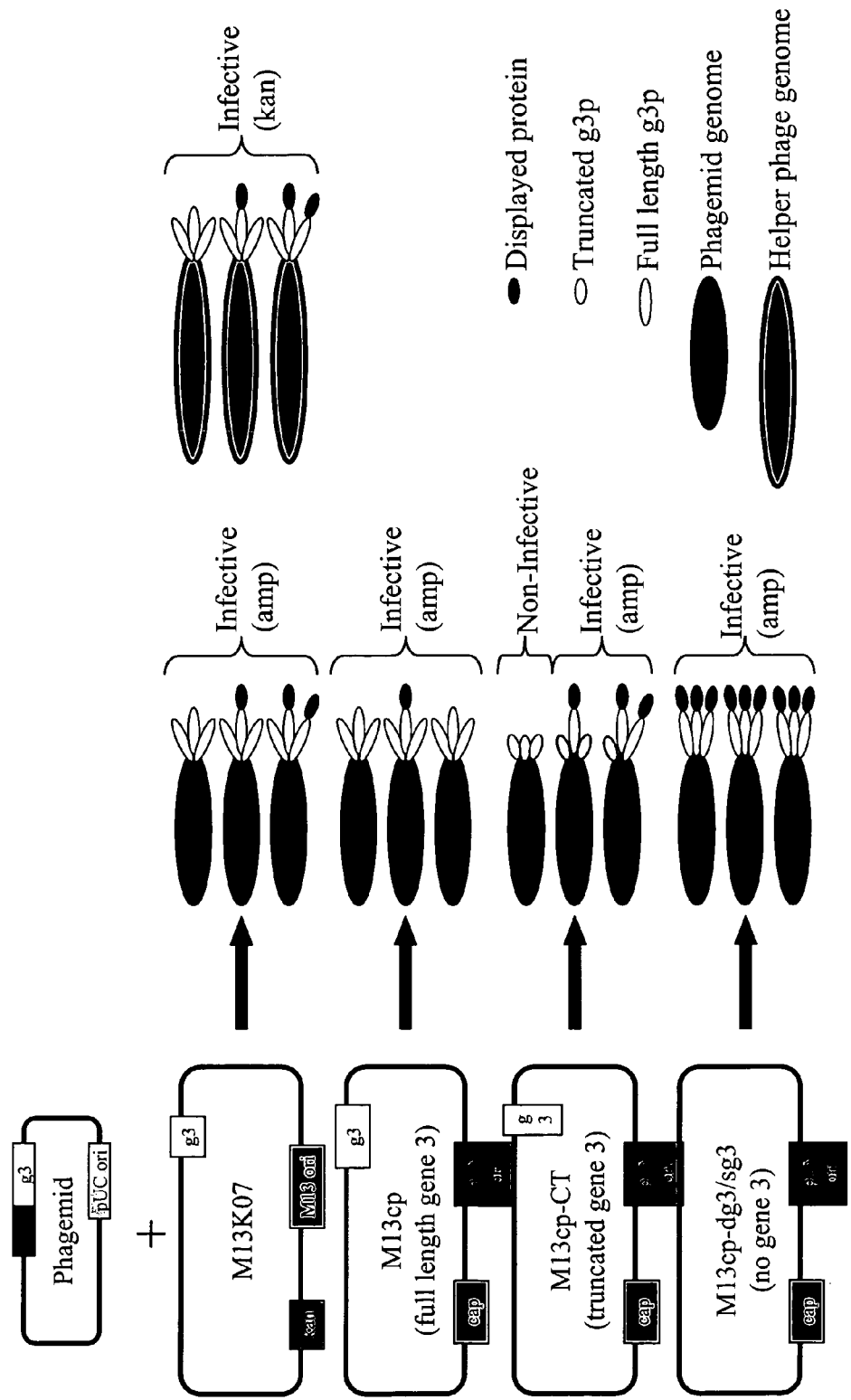
FIG. 1: Phage particle genotypes and phenotypes when using standard phagemid and helper phage systems (top, M13K07), compared with using helper plasmids of the invention (MP13cp, M13cp-CT, and M13cp-dg3/sg3).

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "isolated" and "purified" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

A "filamentous phage genome" is a polynucleotide sequence comprising polypeptide-encoding genes and DNA signals which contains all the necessary information to be packaged into filamentous phage particles when resident in a permissive bacterial cell. Filamentous phage genomes include "natural" or "wild type" phage genomes and derivatives thereof. A "derivative" filamentous phage genome is a polynucleotide sequence comprising polypeptide-encoding genes and DNA signals, which contains (either intrinsically or in combination with one or more genes and fusion protein-coding sequences provided in trans, i.e., via a phagemid) all the necessary information to be packaged into filamentous phage particles when resident in a permissive bacterial cell, in which one or more genetic modifications (i.e., substitutions, deletions, truncations, insertions, frame shifts, stop codons) have been introduced.

A "functionally disabled" gene, protein or polypeptide coding sequence, protein or polypeptide refers to one that does not exert its natural biological function or activity. Thus, for example, a functionally inactivated gene is a gene that cannot be transcribed and/or translated into a protein or polypeptide that exerts the biological function or activity of the protein or polypeptide encoded by the active gene. Inactivation of genes may be accomplished in a number of ways, including without limitation, by deletion, substitution, insertion, mutation, introduction of stop codons or frame shifts, truncation and the like.

Overview and Features of the Invention:

The invention relates to a novel phagemid display system for packaging phagemid DNA into phagemid particles which completely avoids the use of helper phage. The system of the invention incorporates the use of bacterial packaging cell lines which have been transformed with helper plasmids containing all required phage proteins but not the packaging signals. The absence of packaging signals in these helper plasmids prevents their DNA from being packaged in the bacterial cell, which provides a number of significant advantages over the use of both standard[1, 2] and modified helper phages[2, 10-14]. Packaged phagemids expressing a protein or peptide of interest, in fusion with a phage coat protein such as g3p, are generated simply by transfecting phagemid into the packaging cell line.

In one embodiment, the invention provides plasmids comprising a filamentous phage genome or derivative thereof which contains a heterologous origin of replication and in which the phage packaging signal is functionally disabled. The filamentous phage genome or derivative thereof may be derived from any filamentous phage, including without limitation, M13, fd, f1 and IKe as well as derivatives thereof. Suitable origins of replication include, without limitation, p15a, ColE1, pSC101, pMB1, F, R6K and RK2.

The helper plasmids of the invention are useful in the generation of bacterial cells capable of packaging recombinant phagemid when transfected with phagemid DNA, and typically comprise a filamentous phage genome or derivative thereof in which the origin of replication has been replaced by a heterologous replication origin (in one embodiment, belonging to a compatibility group different from the origin used in the phagemid DNA), and in which the phage packaging signal has been deleted or otherwise functionally disabled. A selectable marker such as an antibiotic resistance marker may also be included.

The packaging cell lines of the invention are generated by transforming bacteria with the helper plasmid of interest using standard protocols, and once transformed, are useful for generating pure phagemid particles. Typically, the bacterial cells used for this purpose are *E. coli* cells. In one embodiment described in the Examples, infra, *E. coli* DH5αFT cells are used to generate packaging cell lines. The use of bacteria containing these plasmids completely eliminates the need for helper phage, thereby greatly simplifying phage selection protocols, and enables the development of selection protocols in which display levels are modulated by changing the packaging cell line.

In the practice of the phagemid display methods of the invention, helper plasmids encoding filamentous phage coat proteins, modified coat proteins, truncated or partially deleted coat proteins, and deleted or otherwise functionally disabled coat proteins may be used. In this regard, helper plasmids may incorporate any of the filamentous phage coat proteins, depending upon which of these are fused to proteins of interest in corresponding phagemid DNA vector, and include without limitation g3p, g6p, g7p, g8p and g9p.

As detailed further, infra, helper plasmid encoding full length g3p functions identically to standard helper phage, providing similar phagemid titers and display levels, but without contamination by phage. Helper plasmids containing truncated g3p provide far higher display levels, as assessed by ELISA signals and western blotting, although result in somewhat lower infectious titers. The plasmids without g3p had no apparent advantages over those with truncated g3p.

The phagemid display system of the invention features the complete elimination of helper phage. Thus, there is no need to prepare helper phage or monitor bacterial growth for optimum infectivity by helper phage; phagemid are simply added directly to bacteria at any OD, the bacteria grown, and phage particles are generated. Accordingly, libraries are conveniently generated by transfecting phagemid DNA directly into bacteria containing helper plasmid. This feature of the invention results in a far simpler and more reliable phagemid display system. Another important feature of the invention is the high degree of purity of the phagemid particle preparations made in the packaging cell lines. Contamination with helper phage genome is undetectable in the phagemid display system of the invention. For phage display, this avoids the common problem of helper phage overgrowth, which can result in failed selections. For other applications, the genetic purity of the phagemid particles, combined with their extremely high titers, makes this a powerful method to transfer genetic material between bacteria. It should also facilitate the use of recombinatorial methods to generate antibody diversity[17, 31], by avoiding helper phage amplification between sequential rounds of phagemid recombination and amplification.

In addition, the invention enables selections from both monovalent and multivalent displaying phagemid particles. In general, the phage titers that may be obtained using the system of the invention are similar to those obtained using standard helper phage, and the presence of the helper plasmid in the bacterial cell does not appear to affect the efficiency of transfection with phagemid DNA.

Helper Plasmids Based on M13 and *E. coli* Packaging Cell Lines For Use in M13 Phagemid Display As detailed in the Examples, infra, a number of helper plasmid constructs based on M13mp19 were generated, used to transform *E. coli*, and evaluated for phagemid production and display characteristics. These M13 helper plasmids of the invention replace the M13 phage packaging signal/origin of replication with the p15a origin of replication, and add the chloramphenicol antibiotic resistance gene, and differ in the nature of g3p incorporated therein: the g3 in M13cp is full length, that in M13cp-CT is truncated, containing that portion responsible for phage assembly and release[27, 28], but lacking the domains involved in bacterial toxicity[22, 23], phage infection[24-26] and the inhibition of infection by bacteria carrying p3[2, 18, 19]. M13cp-dg3 and M13cp-sg3 contain no g3, either by virtue of genetic deletion (dg3), or by the inclusion of four non-suppressible stop codons (sg3). Unexpectedly, these latter two helper plasmids exhibited very different properties. Bacteria carrying M13cp-sg3 were poorly infected, and did not appear to display at all— in fact, a positive phagemid ELISA signal using this helper plasmid could not be obtained for any of the scFv tested. *E. coli* transformed with M13cp-dg3, on the other hand, was infected as well as the parent DH5αFT strain, and tended to give titers and ELISA signals only slightly lower than with M13cp-CT-transformed cells. See Example 1, infra.

When phagemid are infected into bacteria containing either of the M13cp and M13cp-sg3 helper plasmids, the titers obtained are consistently lower than those obtained in bacteria containing the other helper plasmids, or no plasmids at all. As this cannot be overcome by increasing the number of bacteria, the problem is not a reduction in infectivity (e.g. by a reduction in the number of bacteria displaying pili), as might be expected, but a failure of these phagemids to establish themselves within the bacteria (e.g. an inability to replicate). The fact this effect is observed with M13cp-sg3, which contains four stop codons in the first 32 amino acids of g3p, and is unable to make g3p, suggests that the inhibition of phagemid replication that these helper plasmids appear to cause is more likely to be mediated at the DNA (or RNA) level than the protein level. Furthermore, the loss of this inhibition in M13cp-CT, which lacks the N terminal domains of g3p, would appear to localize this inhibitory signal to the DNA encoding these domains.

Figure 6:
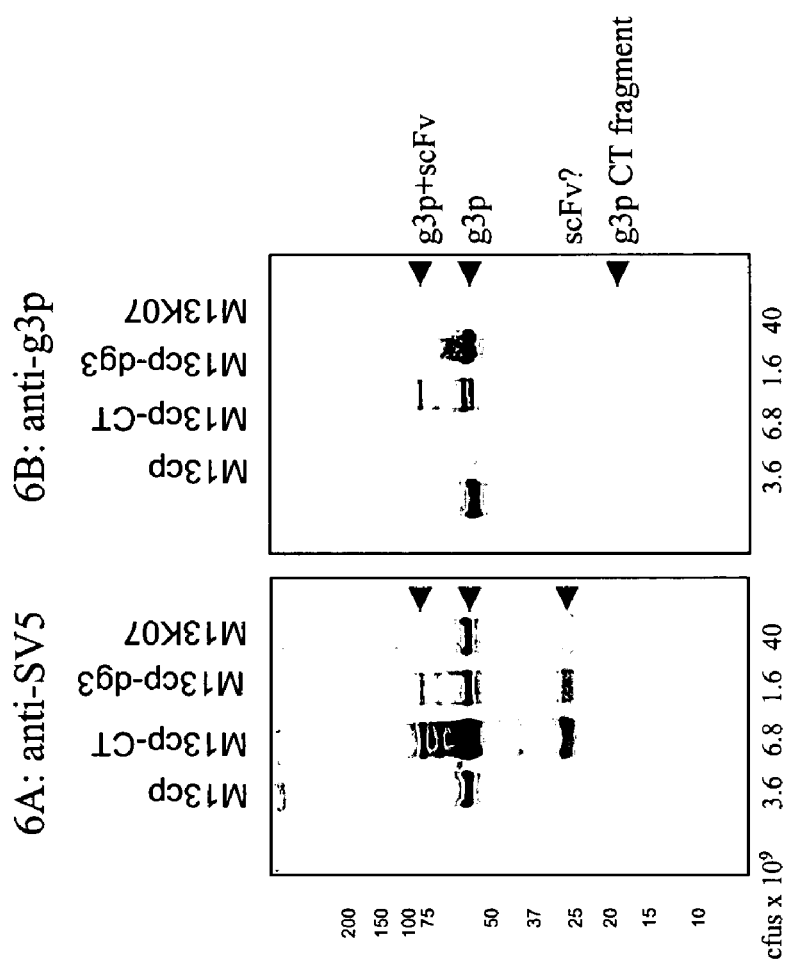
FIG. 6: Western blots of pDAN5-D1.3 phagemid packaged using M13K07 and the different helper plasmids. In 6A the blot was probed with SV5 which recognizes the tag between g3p and D1.3, while in 6B an anti-g3p monoclonal (New England Biolabs) which recognizes a linear epitope in the C terminal domain of g3p, was used.
Figure 7:
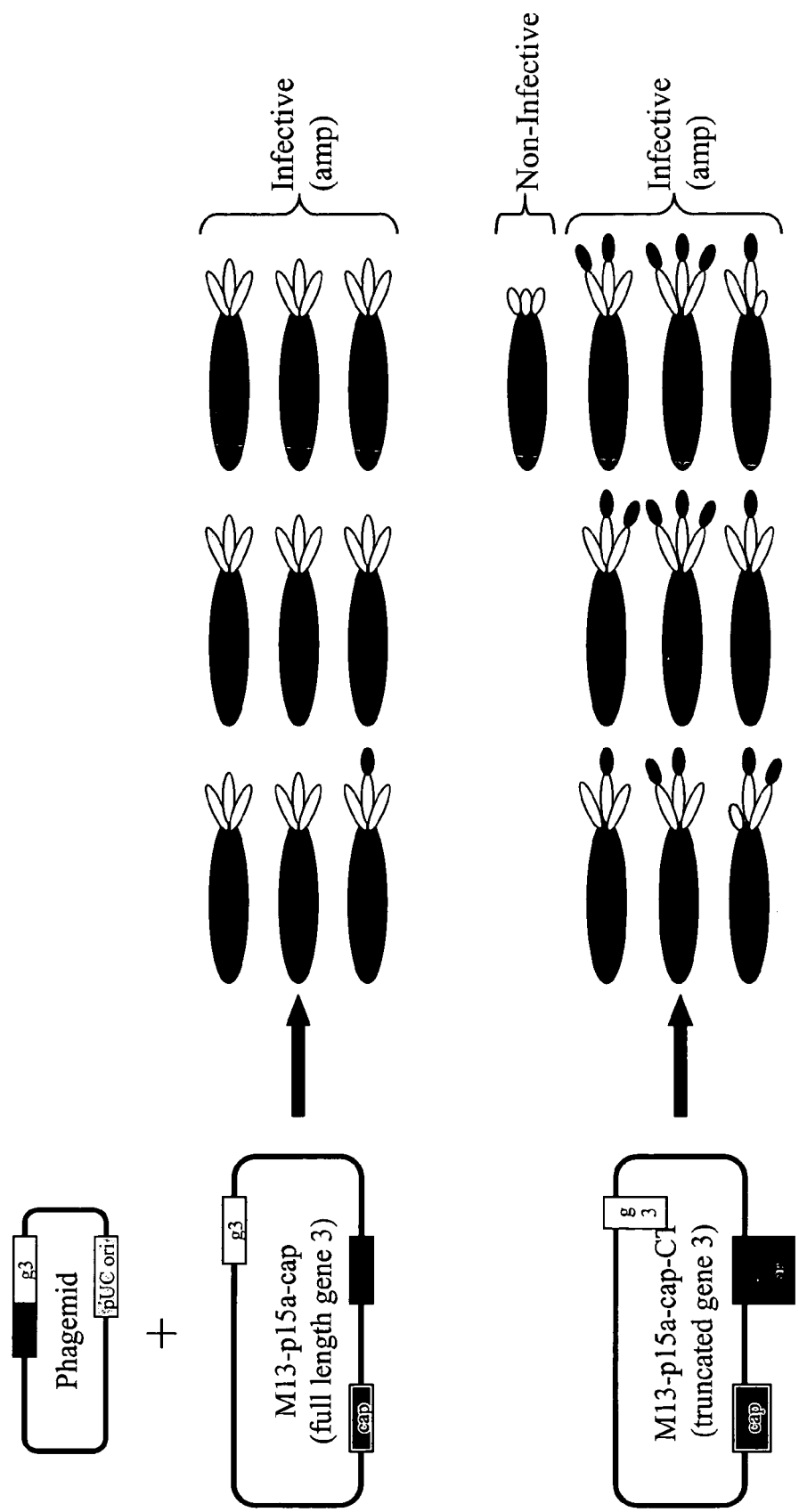
FIG. 7: Representation of phagemid particle phenotype packaged by M13cp and M13 cp-CT.

In phagemid packaged using M13cp most of the g3p appears to be derived from the helper plasmid, and very little from the display vector. As a result, hardly any display occurs (FIG. 6). However, in the case of phagemid particles made using M13cp-CT, over 80% of the incorporated g3p in phagemid is derived from the display vector (compare the intensity of the g3p-CT band in FIG. 6B with that of the g3p and g3p+scFv bands), and of this approximately 50% is full length (compare g3p+scFv with g3p), leading to the very high display levels seen. This indicates there is a preference for the full length g3p provided by the display vector over the truncated form provided by the helper plasmid during phage assembly. Although the C terminal domain is known to be sufficient to allow phage assembly to occur[33], this results suggests that additional portions of g3p may facilitate the process.

M13cp and M13cp-CT, which essentially provide monovalent and multivalent display respectively, stand out as being the most useful helper plasmids, each with potentially different applications. For phage display, it is likely that a selection approach combining both, in which phagemid packaged by M13cp-CT, providing multivalent display able to capture full diversity, is used in early rounds of selection, and M13cp, packaging monovalent phagemids, is used in later rounds to select higher affinity clones, will be the most useful. In addition, M13cp will be very useful for transferring genetic material between bacteria when maximum diversity must be maintained[17, 31], for making phagemid particles when display is not required and when the highest phagemid titers are required. Surprisingly, M13cp-dg3 does not appear to have any advantages over M13cp-CT, giving lower titers, and lower ELISA signals at similar titers.

Although these helper plasmids were designed to lack the M13 packaging signal, the complete absence of packaging into phage particles is at first somewhat surprising, considering that many other plasmids, without M13 origins, do show low levels of packaging[2]. this is usually attributed to the presence of cryptic packaging signals in plasmids which can be inefficiently recognized by the M13 packaging machinery. It is likely that evolution has selected against the presence of other putative packaging sequences in the M13 genome to ensure that only the correct single site is used, so guaranteeing correct orientation within the phage particle[32]. As a result, elimination provides no alternative signals in the phage, and it is clear that neither the p15a origin nor the added antibiotic resistances are able to provide alternative signals.

At a practical level, the M13 helper plasmids are easier to use than systems based on helper phage. Bacteria containing helper plasmid can be either infected or transfected with phagemid and then grown up in selective media without the need to further monitor bacterial OD. In fact, applicants have found that it is sufficient to add phagemid particles to a freshly diluted overnight culture of M13-cap-p15-CT bacteria and grow the bacteria. Bacteria become infected when the culture reaches the appropriate OD, and phage production follows. This will considerably simplify the use of phage display in high throughput antibody selection projects[34-37], where minimal oversight is desired, and it is impractical to closely monitor bacterial OD in order to add helper phage.

EXAMPLES

Various aspects of the invention are further described and illustrated by way of the several examples which follow, none of which are intended to limit the scope of the invention.

Example 1

Construction and Characterization of M13 Helper Plasmids and *E. coli* Phagemid Packaging Cell Lines Materials and Methods:
Cloning:
M13c was created by amplifying M13-mp19 with two outward facing primers, M13 MluI 5' (ttg atg acg cgt cct att ggt taa aaa atg agc tg) [SEQ ID NO: 1] and M13 MluI 3' (ttg atg acg cgt cct aaa tcg gca aaa tcc) [SEQ ID NO: 2] which amplify the whole plasmid and put MluI sites at the junctions between M13 and lac Z. This large PCR product was digested with MluI and the chloramphenicol resistance gene from pBSL121[16] cloned in after cutting with MluI. This produced an M13 phage which confers chloramphenicol resistance.

M13cp was created by amplifying M13c with the two outwards primers, gene 4 3' (cca cac ctg cag cgc tta atg cgc cgc tac agg gcg cgt act) [SEQ ID NO: 3] and CATgene 5' (tga ttt ctg cag acg cgt gtc cga att tct gcc att cat cc) [SEQ ID NO: 4]. These primers amplify the whole plasmid without the M13 origin and place PstI sites at the ends. The p15a origin was amplified from pMPM-K3[16] with 5'P15 ori (taa cgc tgc aga gaa cat ggc ttc atg tgg) [SEQ ID NO: 5] and 3'P15 ori (act gtt ctg cag agc aga cag ttt tat tgt tc) [SEQ ID NO: 6]. This yielded an 875 bp fragment containing the P15 origin of replication flanked by PstI sites which could be cloned into the large M13c PCR fragment using PstI. The complete M13cp plasmid polynucleotide sequence is disclosed in SEQ ID NO: 13, infra.

M13cp-CT was created by amplifying M13cp with two outward primers, g3sig 3' (aca act ttc gga tcc ttc agc gga gtg aga ata g) [SEQ ID NO: 7] and g3D3 5' (ggt ggc tct gga tcc ggt gat ttt gat tat gaa aag) [SEQ ID NO: 8], cleaving with BamHI and religating. These primers are located within g3 and after amplification, the leader of g3 is joined directly to the C terminal domain of g3. The complete M13cp-CT plasmid polynucleotide sequence is disclosed in SEQ ID NO: 14, infra.

M13cp-dg3 was made similarly, using gene 6 5' (cca tat gaa ttc tct att gat tgt gac aaa ata aac tta ttc c) [SEQ ID NO: 9] and gene 8 3' (gaa agg aac aac taa agg aat tcc gaa taa taa ttt ttt cac) [SEQ ID NO: 10] to amplify M13cp. These amplify the whole plasmid without gene 3, and can be ligated using EcoRI. However, the PCR product does include the terminator (T0.25) found at the end of gene 8 and the C terminal portion of gene 3, which is thought to contain the p6 promoter. The complete M13cp-dg3 plasmid polynucleotide sequence is disclosed in SEQ ID NO: 15, infra.

M13cp-sg3 was also made by amplifying the whole of M13cp using g3 stop BclIS (gaa agt tga tca gca taa ccc cat aca tga aat tca ttt act aac gtc) [SEQ ID NO: 11] and g3 stop BclAS (ttt tgc tga tca act ttc aac agt tca agc gga gtg aga ata g) [SEQ ID NO: 12], cutting with BclI and religating. This inserted four stop codons (underlined in the primers) in the first 32 codons of g3. The junctions of all constructs were confirmed by sequencing.

Determination of Infectability:

A single colony starter culture from DH5αF alone, or containing one of the four M13 helper plasmid constructs, was grown overnight at 37° C., 250 rpm, in 2XTY-chloramphenicol in the case of the helper plasmids and 2XTY alone for DH5αF. The following day each culture was diluted and re-grown at 37° C., 250 rpm, to an absorbance $OD_{600}$ of 0.5. As culture growth rates were variable, each culture was stored on ice after reaching $OD_{600}$ 0.5, and for a further 30 minutes after all cultures had reached this absorbance. The samples were then returned to the 37° C. incubator to warm for 30 minutes. Each sample was infected with D1.3 phagemid made from the m13 cp transformation (and so genetically homogenous) at a multiplicity of infection of 1:1 and left to infect for 30 minutes at 37° C. without shaking. Aliquots of infected bacteria were removed from each sample and titered to determine the ability of the bacteria to support phage infection.

Assessment of Phagemid Production:

Transformation: Single colonies were picked from each helper cell construct (m13cp, m13 cp-CT, m13 cp-dg3, and m13 cp-sg3), made chemically competent, and transformed with pDan5-scFv DNA. After growth on 2XTY-ampicillin-chloramphenicol agar plates, colonies from each transformation were picked and grown overnight in 2XTY-ampicillin-chloramphenicol media at 30° C. at 250 rpm.

Infection and direct growth: Bacteria infected as described above at an absorbance of $OD_{600}$ 0.5, were grown overnight at 30° C., 250 rpm, without retention on ice. DH5αF cells containing no helper plasmid were also infected with M13K07 helper phage for an additional 30 minutes at 37° C. without shaking prior to dilution and overnight growth.

Infection and growth from single colony: Single bacterial colonies obtained following a procedure similar to that described for titration above were picked and grown overnight in 2XTY-ampicillin-chloramphenicol at 30° C., 250 rpm.

For each phage production protocol, after overnight growth phagemids were collected from the supernatant by centrifugation (4000 rpm, 30 min), and the levels of phage production determined by titration in DH5αF cells plated on both 2XTY-ampicillin and 2XTY-chloramphenicol plates.

Results

Helper Plasmids Containing Full Length q3p:

Various helper plasmids which can reside within *E. coli* bacteria and provide all the packaging functions of helper phage without the need for infection by helper phage were constructed as described, supra. In a first construct, the M13 polylinker and lac gene were replaced by the chloramphenicol resistance gene[16]. In a second construct (M13cp), the M13 origin of replication was replaced by the p15a origin, which, as it belongs to a different incompatibility group to pUC, should allow it to co-exist with standard pUC based phagemid display vectors. As a single restriction site was utilized for each cloning, it should have been possible to clone both the p15a origin and the chloramphenicol resistance gene in two orientations. However, only a single orientation for each was obtained, and this was used for further constructs. DH5αFT *E. coli* bacteria containing these plasmids were transformed with a standard phagemid display vector (pDAN5-D1.3[17], which displays an scFv recognizing lysozyme) and tested for their ability to produce phage particles carrying ampicillin resistance. Table 2A shows that although both plasmids were able to supply all the necessary phage proteins to produce phagemid particles carrying ampicillin resistance, M13c (which still contains the M13 packaging signal) was, not surprisingly, packaged in preference to the phagemid. This resulted in chloramphenicol titers which were 10,000 fold higher than the ampicillin titers. The construct containing the p15a origin (M13cp), however, had ampicillin titers comparable to those obtained using standard helper phage, but with undetectable chloramphenicol titers (<5 cfu/ml), demonstrating that this helper plasmid, unlike standard helper phage, is unable to package itself. This showed that the concept of a bacterial packaging cell line in which all the helper phage functions were resident on a compatible, non-packagable, plasmid, rather than infected as a helper phage, was valid, and was able to produce titers as good as standard helper phage infection.

The next step was to determine whether the presence of such a helper plasmid within bacteria reduced their infectability. This is important if selection outputs are to be infected directly into such cells. Phagemid particles prepared using the M13cp helper plasmid, and therefore genetically homogenous, were infected into DH5αFT, or DH5αFT containing M13cp or DH5αFT containing standard M13K07 helper phage. The results in Table 2B show that although the phage could infect DH5αFT very efficiently, their ability to infect in the presence of M13cp was consistently reduced by five to ten fold, and by approximately 1000 fold if M13K07 was present. Initially, it was assumed that this was due to the presence of the N terminal portion of p3, which when expressed in bacteria, has been shown to reduce bacterial infectivity[2, 18, 19]. However, the reduced infection rates when M13cp is present, relative to DH5αFT alone, could not be overcome by increasing the number of bacteria available for infection, modifying antibiotic concentrations, changing the OD at which infection occurred, or the temperature at which bacteria were grown after infection, suggesting that the problem is related to survival and replication of phagemid DNA within bacteria after entry, rather than phagemid entry itself.

Helper Plasmids Containing Truncated or Deleted g3p:

In addition to the inhibition of infection by filamentous phage, g3p has significant additional pleiotropic effects on *E. coli*, including resistance to colicins[19-21], inhibition of conjugation[18], the induction of periplasmic protein release[18,22], increased detergent sensitivity[18, 19] and the formation of pores[23]. Most of these are mediated by the two N terminal domains, which are also responsible for binding to the F pilus and interacting with tolA[24-26]. The C terminal domain, in contrast, is responsible for viral assembly and release[27, 28], and although phage containing only this domain can be assembled, they are completely non-infectious. As a result, the elimination of either the whole of g3p, or the N terminal domains from the helper plasmid, will result in phagemid particles in which only those containing full length g3p supplied by the recombinant g3p in the display phagemid, would be infectious. This should result in operational advantages, such as increased display levels and the reduction of background due to the inability of non-displaying phage to propagate. In addition, such constructs may also improve the survival of phagemids within bacteria if g3p is involved. In order to study this, three additional constructs were made. In the first (M13cp-CT), the N terminal two domains of g3p were removed, leaving only the C terminal domain connected to the leader sequence; in the other two, g3 was inactivated, either by deletion (M13cp-dg3) or by the insertion of four non-suppressible stop codons within the first 32 codons of g3 (M13cp-sg3), in a fashion similar to that used to make Exphage[13] and Phaberge[11]. The expected phenotype of the phage produced by these helper plasmids is illustrated in FIG. 1.

Figure 2B:
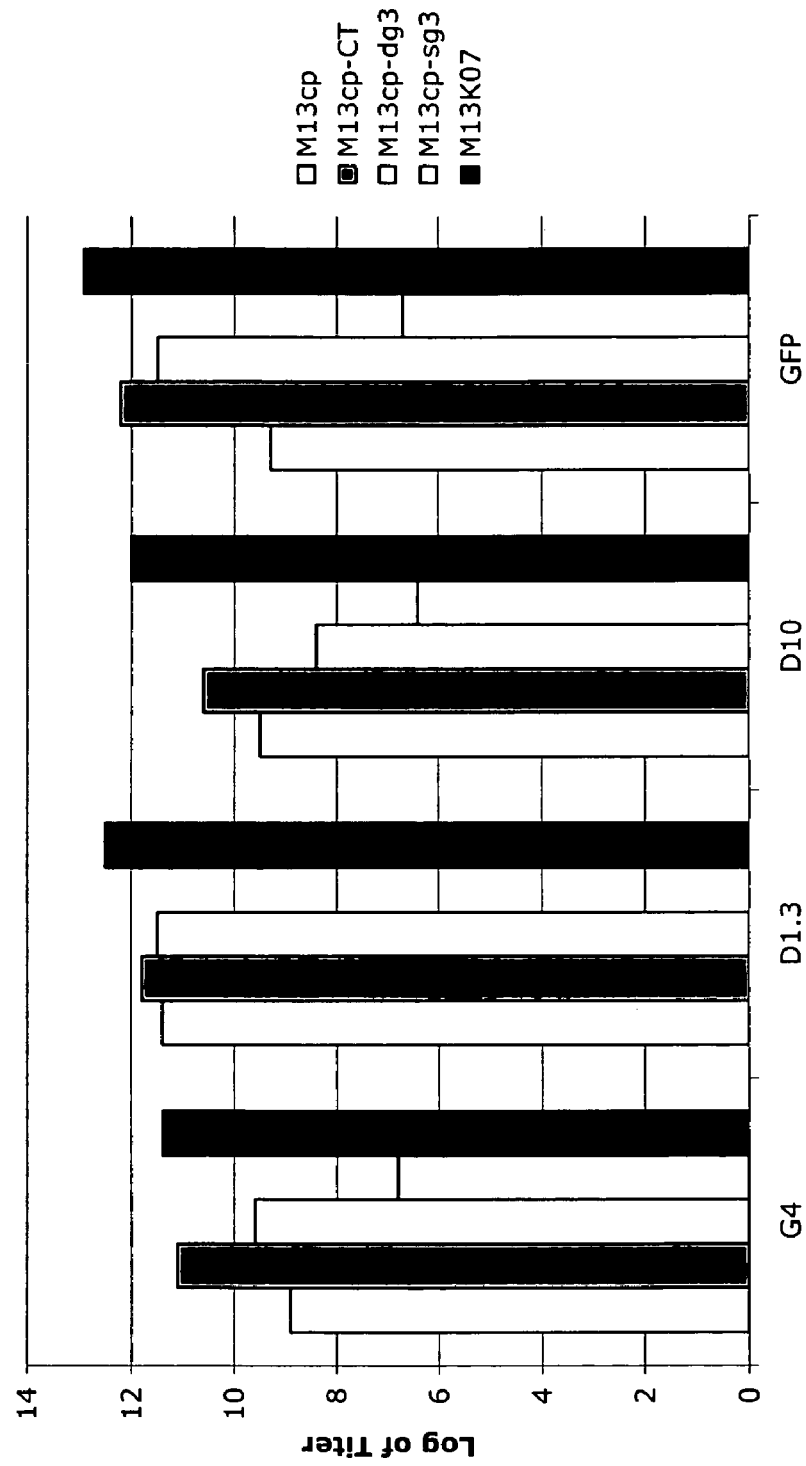
FIG. 2B: DH5αFT bacteria containing each of the helper plasmids were infected with a genetically homogenous preparation of the different scFv phage indicated (previously prepared using M13cp) and bacterial cultures allowed to grow overnight. The titers of the different phagemid preparations were then assessed by infection into DH5αFT.

The ability of these helper plasmids to package pDAN5-D1.3 was tested under three different conditions: 1) by transfecting pDAN5-D1.3 DNA into bacteria containing each of the helper plasmids, plating on ampicillin/chloramphenicol plates, picking a single colony and growing overnight; 2) by infecting bacteria containing the helper plasmids with genetically homogenous pDAN5-D1.3 phagemid (previously created using M13cp) and growing directly overnight without plating; and 3) by infecting bacteria containing the helper plasmids with pDAN5-D1.3 phagemid, plating on ampicillin/chloramphenicol plates, picking a single colony and growing overnight. The results shown in FIG. 2A indicate that M13cp produces titers within an order of magnitude to those obtained by standard helper phage in all conditions except one: if genetically homogenous phagemid are infected into M13cp bacteria and grown directly, the titer is approximately 500-fold less. An examination of phage production from a single colony after transformation or infection, shows that, in general, titers are better after infection and that there is a five to ten fold reduction in titer from M13cp to M13cp-CT. The reduced titer of the M13cp-CT produced phage is not surprising, since, like the CT helper phage described by Kramer et al.,[14] the majority of phage contain deleted g3p derived from the helper phage and so are unable to infect, and only those phage which display the recombinant protein (and hence contain full length g3p) are infectious. The phage titers produced by bacteria in which g3 was eliminated from the helper plasmid by deletion (M13cp-dg3) were a further 5-10 fold lower, while those produced by the bacteria in which g3 contained the four stop codons were an additional 100-10,000 fold lower.

To see whether different phagemid constructs gave similar results, a number of different scFvs as well as GFP were also displayed. In this case, titers were determined from phagemid prepared after infection and growth overnight, without intermediate plating (condition 2 above). Although this is known to give lower titers for phagemid prepared using M13cp (FIG. 2A), the trend obtained for the different scFvs and GFP (FIG. 2B) is similar to that previously obtained with D1.3, indicating that these helper plasmids are as generally functional as M13K07 has proved to be.

Figure 3:
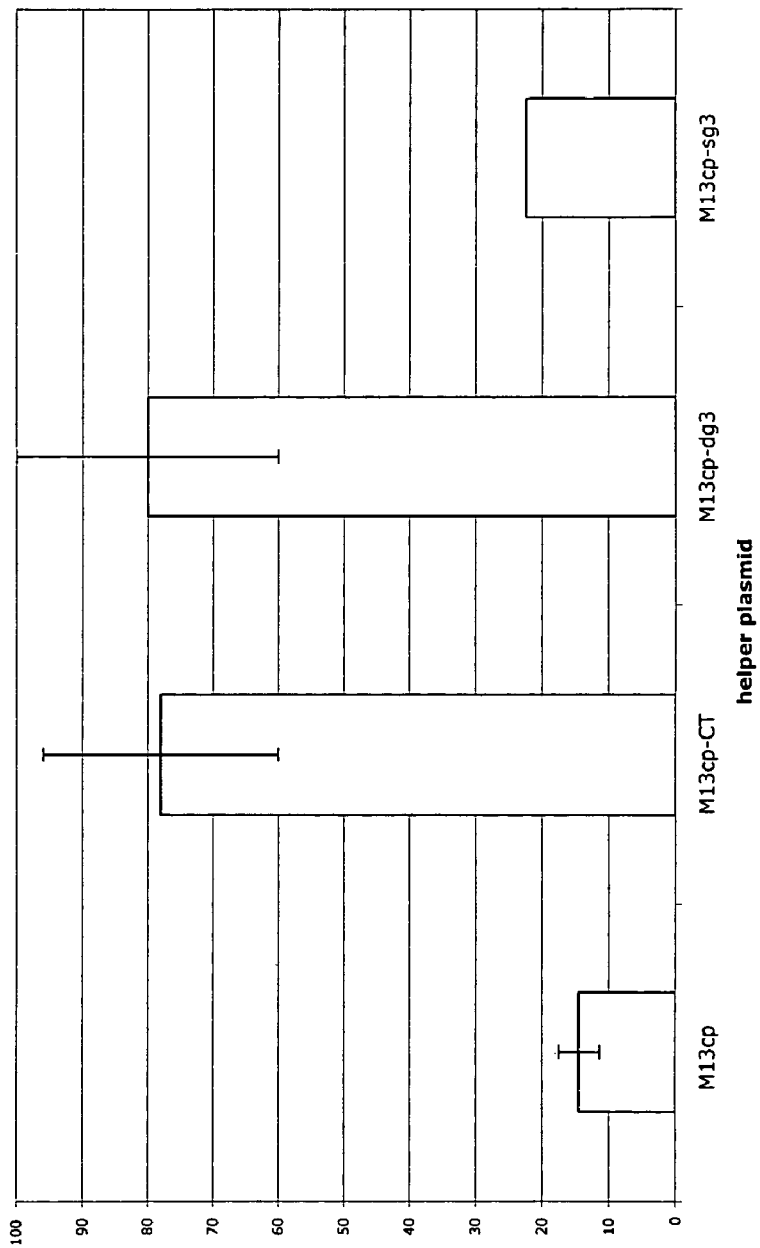
FIG. 3: DH5αFT bacteria containing each of the helper plasmids were infected with a genetically homogenous preparation of D1.3 phagemid (previously prepared using M13cp) and the titers obtained are expressed as a percentage of the titers obtained using DH5αFT. Error bars indicate the range of results obtained.

We have shown above (Table 2B) that when bacteria contain M13cp, they are less able to support phagemid replication, and as a result give apparent phage titers which are approximately ten fold less than bacteria containing no helper plasmid. To determine whether the other helper plasmids also had deleterious effects on bacterial infectability or phagemid survival, phagemid displaying D1.3 were infected into DH5αFT containing each of the helper plasmids. The results (in FIG. 3) expressed as a percentage of true titer, where true titer is that obtained when infecting into DH5αFT containing no additional plasmids, show that DH5αFT containing helper plasmid with full length g3p (M13cp) or g3 inactivated by stop codons (M13cp-sg3) are consistently infected less efficiently than DH5αFT containing helper plasmids with either deleted (M13cp-dg3) or truncated (M13cp-CT) g3p, both of which give titers very similar to those obtained in DH5αFT.

Figure 4:
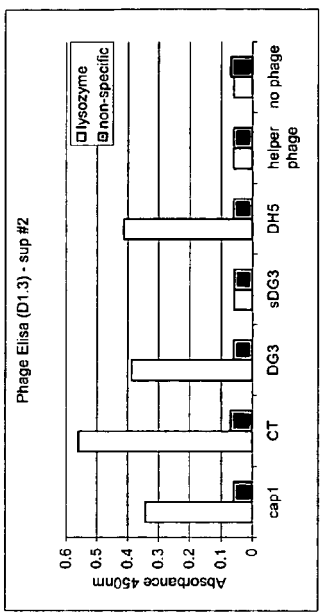
FIG. 4: Phage ELISA signals obtained with two different preparations of three different scFvs (D1.3, recognizing lysozyme; anti-ubiquitin; and F10, recognizing the *Y. pestis* f1 antigen) prepared using each of the different helper plasmids. An anti-g8p monoclonal labeled with horse radish peroxidase (New England Biolabs) was used as the secondary antibody.
Figure 4:
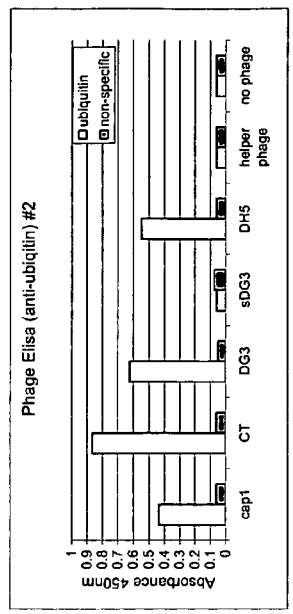
Figure 4:
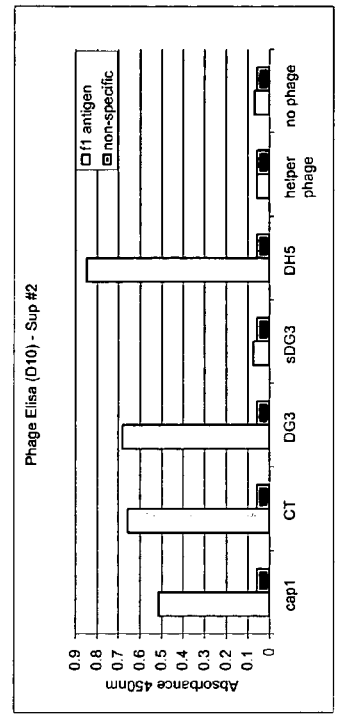
Figure 4:
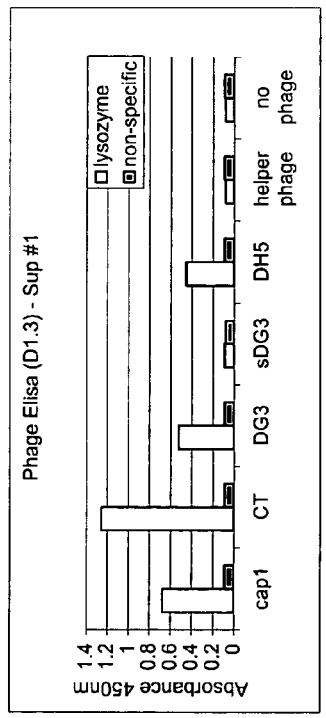
Figure 4:
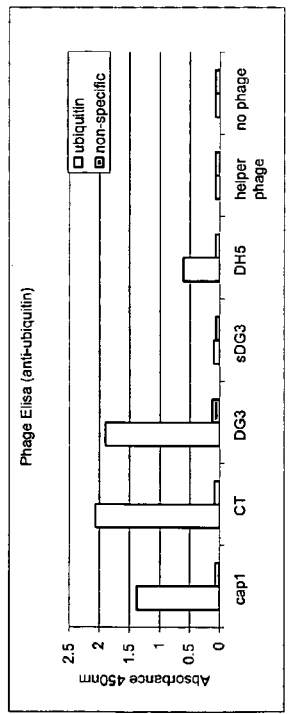
Figure 4:
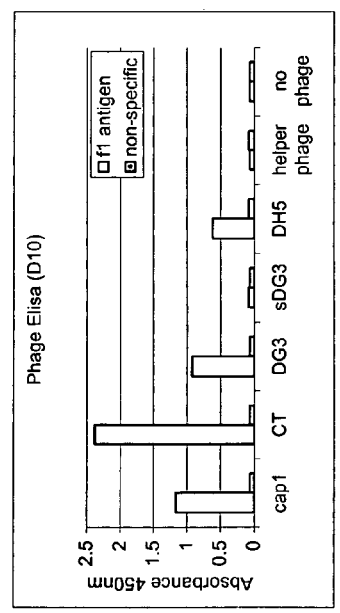

Assessing Display Levels:

The most stringent assessment of functional display is to carry out phage ELISAs, since only well displayed and correctly folded scFvs will provide positivity in a phage ELISA. In order to provide practical comparisons, phage ELISAs were carried out for three different scFvs using growth supernatants directly after preparation, without purification or concentration by PEG precipitation. Comparing the signals for the three scFvs, in duplicate, with the four different display systems shows (FIG. 4) that the truncated (CT) helper plasmid provides the highest ELISA signal in all cases except one. Although there is some variation in the remaining ELISAs, the standard helper phage, full length g3 and deleted g3 helper plasmids give approximately similar signals, while the helper plasmid based on the inactivation of g3 with stop codons was consistently negative.

Figure 5:
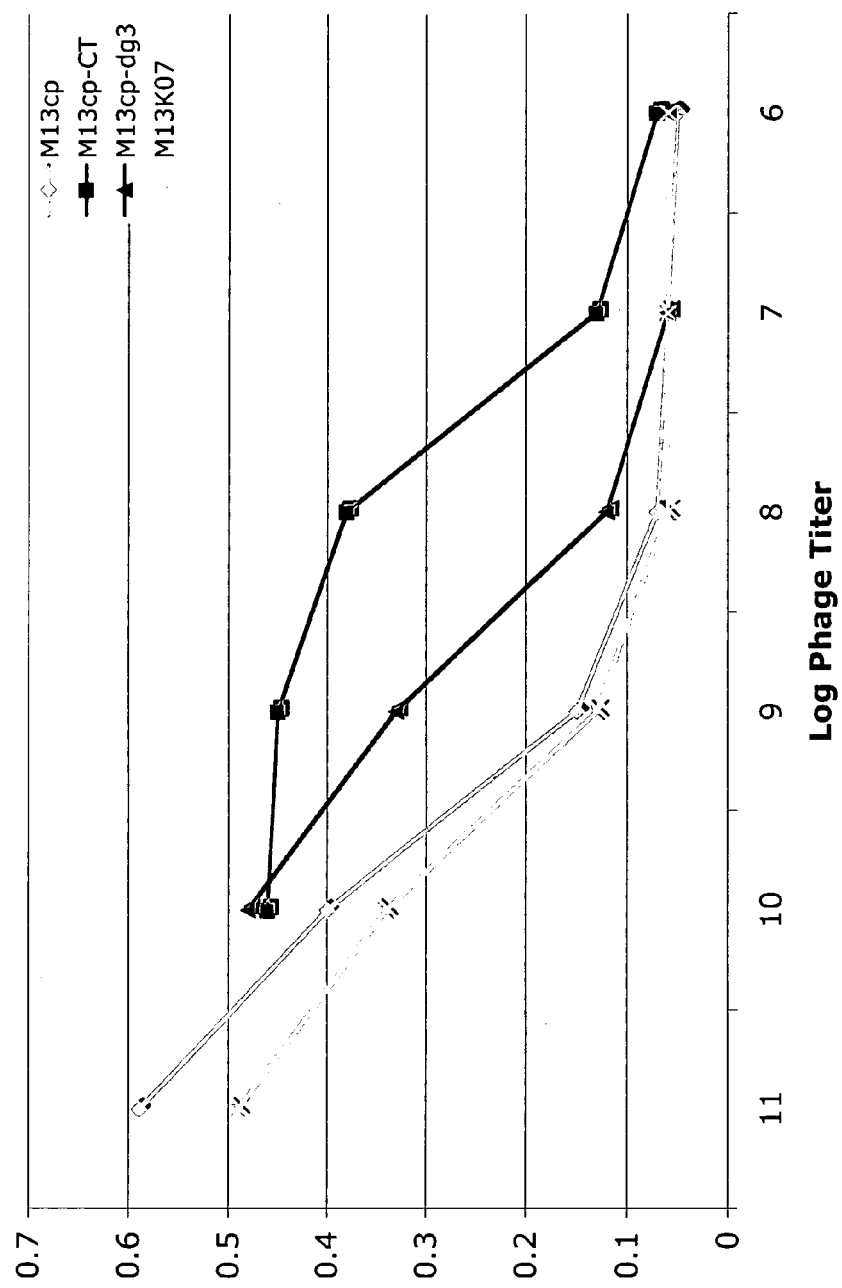
FIG. 5: Phage ELISA signals plotted against phagemid titer for pDAN5-D1.3 phagemid packaged using M13K07 and the three different helper plasmid constructs.

The ELISA signals obtained with the pDAN5-D1.3 phagemid prepared using the different helper plasmids were also assessed in terms of the signal obtained at different defined phage titers. The results in FIG. 5 show that M13cp-CT produces the most active phage, with similar ELISA signals obtained with ten fold less phage than M13cp-dg3 and approximately one hundred fold less phage than M13cp or standard helper phage.

D1.3 phage were also examined by western blot, using an anti-g3p antibody and the SV5 antibody[30], which recognizes the tag placed between the displayed protein and g3p. As the latter will only recognize recombinant g3p from the display vector, it will give an assessment of the total amount of incorporated recombinant g3p (equivalent to the sum of the g3p+scFv and g3p bands derived from the proteolytic degradation of g3p+scFv) as well as that portion which is full length and displaying scFv (the g3p+scFv band). In these experiments phage were not normalized for titer, but culture volume, giving an indication of how much recombinant protein will be displayed under standard use, with the actual numbers of phage loaded indicated.

The results (FIG. 6) show again that truncated g3 gives the highest display level, as shown by the intensity of the g3p+scFv band, even though the number of phage loaded is five fold less than those produced using standard helper phage. The helper plasmid lacking g3 also gave good display, while very little full length display was visible with either M13cp or M13K07 packaged phagemid particles. A similar western blot was carried out using an anti-g3p monoclonal (New England Biolabs) which recognizes the C terminal portion of g3p. This will reveal all g3p, whether derived from phagemid or helper plasmid, including the truncated g3p (as a band of 19 kDa). This clearly shows that more than 80% of the p3 incorporated using M13cp-CT is derived from the recombinant phagemid g3p (compare the intensity of the truncated g3p band—derived from the helper plasmid—with that of the g3p and g3p+scFv bands). Interestingly, the amount of total recombinant phagemid g3p incorporated in M13cp-dg3, M13cp and M13K07 appears to be similar (FIG. 6A), however, while functional display (g3p+scFv band) can be seen for M13cp-dg3, none is visible for M13cp and M13K07.

TABLE 2A

Titers of ampicillin, kanamycin and chloramphenicol colony forming units (cfus) when pDAN5-D1.3 is packaged using M13-cap, M13-cap-p15 or standard helper phage.

| Helper plasmid/phage | Amp | Kan | Cap |
|---|---|---|---|
| M13c | $1 \times 10^6$ | ND | $2 \times 10^{10}$ |
| M13cp | $1.1 \times 10^{12}$ | ND | 0 |
| M13K07 | $1 \times 10^{12}$ | $8 \times 10^9$ | ND |

TABLE 2B

The number of colonies formed when a constant number of pDAN5-D1.3 phagemid particles carrying ampicillin resistance are infected into DH5αFT containing no plasmid (which should represent the true cfu titer of the phagemid prep), M13-cap-p15 or standard M13K07 helper phage.

| | Exp 1 | Exp 2 |
|---|---|---|
| DH5αFT | $1.4 \times 10^8$ | $4 \times 10^8$ |
| M13cp | $1.4 \times 10^7$ | $7 \times 10^7$ |
| M13K07 | $1.6 \times 10^5$ | ND |

TABLE 1

DIFFERENT HELPER PHAGE SYSTEMS

| Mutation/mechanism | [1]Helper phage titers/ml | Display levels | [1,2]Rescued phagemid titers/ml | Use in display | Helper phage propagation | Reference and helper phage name |
|---|---|---|---|---|---|---|
| | $10^{11}$ | Low | $2 \times 10^{10-11}$ | Standard infection | Growth | M13K07[3] |
| Trypsin site in g3p, elution with trypsin | $10^{11}$ | Low | $2 \times 10^{10-11}$ | Standard infection | Growth | KM13[15] |
| g3 deletion | $10^{5-6}$ | High | ~$10^{10}$ | Standard infection | g3 plasmid expression under lac promoter | 38 |
| g3 deletion | $2 \times 10^9$ | NT | $10^9$ | Standard infection | g3p plasmid expression | M13MD□3.2[10] |
| g3 deletion[4] | $10^{10}$ | NT | NT | Standard infection | g3p plasmid expression under pspA promoter | R408d3[2] |
| g3 deletion (8-406) | $10^9$ | High | $10^{9-10}$ | Standard infection | g3p integrated into E. coli genome | Hyperphage[12] |
| g3 N1 & N2 domains deleted[5] | $3 \times 10^{11}$ | Low | $10^{11}$ total $5 \times 10^8$ infective | Standard infection | g3p plasmid expression | CT helper phage[14] |
| Amber stop codon 5' g3 | [6]$10^{12-13}$ | High | $10^{10-11}$ | Non-suppressor strain | Suppressor strain | Ex-phage[13] |
| Amber stop codon 3' g3 | $10^{11}$ | High | $10^{9-10}$ | Non-suppressor strain | Suppressor strain | Phaberge[11] |

NT—not tested
[1]titers are unconcentrated supernatant titers - i.e. not PEG precipitated
[2]refers to the number of infectious phagemid particles, independent of whether they carry antibody or no
[3]data from our laboratory
[4]some reversion due to packaging of plasmid expressing p3 observed - probably also occurs in other plasmid expression systems, but not examined
[5]rescued phagemid are two populations, displaying and infective, non displaying and non-infective
[6]standard M13K07 titers obtained in this laboratory tend to be 10-100 fold higher than obtained elsewhere

TABLE 3

Summary of helper plasmid characteristics

| Helper plasmid | Form g3p | Phage production titer | Infectability of bacteria bearing plasmid | Notes | Example use |
|---|---|---|---|---|---|
| M13cp | Full length | Equal M13K07 | 10% DH5αFT | Most similar to phage produced using helper phage | Transfer genetic material. Monovalent phage display. |
| M13cp-CT | Truncated | 5-20% M13K07 | Equal DH5αFT | Behaves more like g3p deletion. Only phagemid with recombinant g3p are infectious | Multivalent phage display |
| M13cp-dg3 | Absent | 0.1-10% M13K07 | Equal DH5αFT | All phage produced have recombinant g3p | Multivalent phage display |

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

LITERATURE CITED

1. Yanisch, P.C., Vieira, J. & Messing, J. Improved M13 phage cloning vectors and host strains: nucleotide sequences of the M13mp18 and pUC19 vectors. *Gene* 33, 103-119 (1985).
2. Rakonjac, J., Jovanovic, G. & Model, P. Filamentous phage infection-mediated gene expression: construction and propagation of the gill deletion mutant helper phage R408d3. *Gene* 198, 99-103 (1997).
3. Hoogenboom, H. R. et al. Multi-subunit proteins on the surface of filamentous phage: methodologies for displaying antibody (Fab) heavy and light chains. *Nucleic Acids Res.* 19, 4133-4137 (1991).
4. Huie, M. A. et al. Antibodies to human fetal erythroid cells from a nonimmune phage antibody library. *Proc. Natl. Acad. Sci. U.S.A.* 98, 2682-2687 (2001).
5. Clackson, T. & Wells, J. A. In vitro selection from protein and peptide libraries. *TIBTECH* 12, 173-184 (1994).
6. Schier, R. et al. Isolation of high-affinity monomeric human anti-c-erbB-2 single chain Fv using affinity-driven selection. *J. Mol. Biol.* 255, 28-43 (1996).
7. Schier, R. & Marks, J. D. Efficient in vitro affinity maturation of phage antibodies using BIAcore guided selections. *Hum Antibodies Hybridomas* 7, 97-105 (1996).
8. Schier, R. et al. Isolation of picomolar affinity anti-c-erbB-2 single-chain Fv by molecular evolution of the complementarity determining regions in the center of the antibody binding site. *J. Mol. Biol.* 263, 551-567 (1996).
9. Yang, W. P. et al. CDR walking mutagenesis for the affinity maturation of a potent human anti-HIV-1 antibody into the picomolar range. *J. Mol. Biol.* 254, 392-403 (1995).
10. Duenas, M. & Borrebaeck, C. A. Novel helper phage design: intergenic region affects the assembly of bacteriophages and the size of antibody libraries. *FEMS Microbiol Lett* 125, 317-321 (1995).
11. Soltes, G. et al. A new helper phage and phagemid vector system improves viral display of antibody Fab fragments and avoids propagation of insert-less virions. *J Immunol Methods* 274, 233-244 (2003).
12. Rondot, S., Koch, J., Breitling, F. & Dubel, S. A helper phage to improve single-chain antibody presentation in phage display. *Nat Biotechnol* 19, 75-78 (2001).
13. Baek, H., Suk, K. H., Kim, Y. H. & Cha, S. An improved helper phage system for efficient isolation of specific antibody molecules in phage display. *Nucleic Acids Res* 30, e18 (2002).
14. Kramer, R. A. et al. A novel helper phage that improves phage display selection efficiency by preventing the amplification of phages without recombinant protein. *Nucleic Acids Res* 31; e59 (2003).
15. Jestin, J. L., Volioti, G. & Winter, G. Improving the display of proteins on filamentous phage. *Res Microbiol* 152, 187-191 (2001).
16. Alexeyev, M., Shokolenko, I. & Croughan, T. Improved antibiotic-resistance gene cassettes and omega elements for *Escherichia coli* vector construction and in vitro deletion/insertion mutagenesis. *Gene* 160, 63-67 (1995).
17. Sblattero, D. & Bradbury, A. Exploiting recombination in single bacteria to make large phage antibody libraries. *Nat. Biotechnol.* 18, 75-80 (2000).
18. Boeke, J. D., Model, P. & Zinder, N. D. Effects of bacteriophage f1 gene III protein on the host cell membrane. *Mol Gen Genet* 186, 185-192 (1982).
19. Stengele, I., Bross, P., Garces, X., Giray, J. & Rasched, I. Dissection of functional domains in phage fd adsorption protein. Discrimination between attachment and penetration sites. *J Mol Biol* 212, 143-149 (1990).
20. Zinder, N. D. Resistance to colicins E3 and K induced by infection with bacteriophage f1. *Proc Natl Acad Sci USA* 70, 3160-3164 (1973).
21. Smilowitz, H. Bacteriophage f1 infection and colicin tolerance. *J Virol* 13, 100-106 (1974).
22. Rampf, B., Bross, P., Vocke, T. & Rasched, I. Release of periplasmic proteins induced in *E. coli* by expression of an 23. N-terminal proximal segment of the phage fd gene 3 protein. *FEBS Lett* 280, 27-31 (1991).
23. Glaser-Wuttke, G., Keppner, J. & Rasched, I. Pore-forming properties of the adsorption protein of filamentous phage fd. *Biochim Biophys Acta* 985, 239-247 (1989).
24. Riechmann, L. & Holliger, P. The C-terminal domain of TolA is the coreceptor for filamentous phage infection of *E. coli. Cell* 90, 351-360 (1997).
25. Karlsson, F., Borrebaeck, C. A., Nilsson, N. & Malmborg-Hager, A. C. The mechanism of bacterial infection by filamentous phages involves molecular interactions between TolA and phage protein 3 domains. *J Bacteriol* 185, 2628-2634 (2003).
26. Lubkowski, J., Hennecke, F., Pluckthun, A. & Wlodawer, A. Filamentous phage infection: crystal structure of g3p in complex with its coreceptor, the C-terminal domain of TolA. *Structure Fold Des* 7, 711-722 (1999).
27. Davis, N. G. & Model, P. An artificial anchor domain: hydrophobicity suffices to stop transfer. *Cell* 41, 607-614 (1985).
28. Davis, N. G., Boeke, J. D. & Model, P. Fine structure of a membrane anchor domain. *J Mol Biol* 181, 111-121 (1985).
29. Sidhu, S. S., Lowman, H. B., Cunningham, B. C. & Wells, J. A. Phage display for selection of novel binding peptides. *Methods Enzymol* 328, 333-363 (2000).
30. Hanke, T., Szawlowski, P. & Randall, R. E. Construction of solid matrix-antibody-antigen complexes containing simian immunodeficiency virus p27 using tag-specific monoclonal antibody and tag-linked antigen. *J. Gen. Virol.* 73, 653-660 (1992).
31. Sblattero, D., Lou, J., Marzari, R. & Bradbury, A. In vivo recombination as a tool to generate molecular diversity in phage antibody libraries. *J. Biotechnol.* 74, 303-315 (2001).
32. Marvin, D. A. Filamentous phage structure, infection and assembly. *Curr Opin Struct Biol* 8, 150-158 (1998).
33. Rakonjac, J., Feng, J. & Model, P. Filamentous phage are released from the bacterial membrane by a two-step mechanism involving a short C-terminal fragment of pIII. *J Mol Biol* 289, 1253-1265 (1999).
34. Bradbury, A. et al. Antibodies in proteomics I: generating antibodies. *Trends Biotechnol* 21, 275-281 (2003).
35. Bradbury, A. et al. Antibodies in proteomics II: screening, high-throughput characterization and downstream applications. *Trends Biotechnol* 21, 312-317 (2003).
36. Walter, G., Konthur, Z. & Lehrach, H. High-throughput screening of surface displayed gene products. *Comb Chem High Throughput Screen* 4, 193-205 (2001).
37. Hallborn, J. & Carlsson, R. Automated screening procedure for high-throughput generation of antibody fragments. *Biotechniques Suppl*, 30-37 (2002).
38. Griffiths, A. D. et al. Human anti-self antibodies with high specificity from phage display libraries. *EMBO J.* 12, 725-734 (1993).

What is claimed is:

1. A plasmid comprising an M13 phage genome, wherein the M13 phage genome comprises a heterologous origin of replication and a functionally disabled phage packaging signal, and wherein (1) the g3p gene of the M13 phage genome encodes a protein in which amino acid residues 21-273 are deleted; (2) the g3p gene of the M13 phage genome is inactivated by the introduction of stop codons within the g3p gene at codons 20, 25, 28 and 30; or (3) the g9p gene of the M13 phage genome is inactivated by the introduction of a stop codon within the g9p gene at codon 6.

2. The plasmid according to claim 1, further comprising a selectable marker gene.

3. The plasmid according to claim 2, wherein the selectable marker gene is an antibiotic resistance gene.

4. The plasmid according to claim 1, wherein the origin of replication is selected from the group consisting of p15a, ColE1, pSC101, pMB1, F, R6K and RK2.

5. The plasmid according to claim 1, wherein the g3p gene encodes a protein in which amino acid residues 21-273 are deleted.

6. The plasmid according to claim 1, wherein the g3p gene is inactivated by the introduction of stop codons within the g3p gene at codons 20, 25, 28 and 30.

7. The plasmid according to claim 1, wherein the g9p gene is inactivated by the introduction of a stop codon within the g9p gene at codon 6.

8. The plasmid according to claim 1, wherein the M13 phage genome is an M13mp19 phage genome.

9. The plasmid according to claim 1, comprising the nucleotide sequence of SEQ ID NO. 13.

10. The plasmid according to claim 1, comprising the nucleotide sequence of SEQ ID NO. 14.

11. The plasmid according to claim 1, comprising the nucleotide sequence of SEQ ID NO. 15.

12. A bacterial cell containing the plasmid of claim 1.

13. A bacterial cell containing the plasmid of claim 8.

14. A bacterial cell containing the plasmid of claim 9.

15. A bacterial cell containing the plasmid of claim 10.

16. A bacterial cell containing the plasmid of claim 11.

17. A plasmid comprising an M13 phage genome, wherein the M13 phage genome comprises a heterologous origin of replication and a deleted phage packaging signal, and wherein (1) the g3p gene of the phage genome encodes a full-length g3p protein; (2) the g3p gene of the phage genome is deleted; (3) the g3p gene of the phage genome encodes a g3p protein in which amino acids 21-273 are deleted; or (4) the g3p gene of the phage genome is functionally inactivated by the introduction of stop codons within the g3p gene at codons 20, 25, 28 and 30.

18. The plasmid according to claim 17, further comprising an antibiotic resistance gene.

19. A plasmid comprising an M13 phage genome, wherein the M13 phage genome comprises a heterologous origin of replication and a deleted phage packaging signal, wherein the heterologous origin of replication is a p15a origin of replication.

20. The plasmid of claim 19, wherein the g3p gene of the M13 phage genome encodes a full-length g3p protein.

21. The plasmid of claim 19, wherein the g3p gene of the M13 phage genome is deleted.

22. The plasmid of claim 19, wherein the g3p gene of the M13 phage genome encodes a g3p protein in which amino acids 21-273 are deleted.

23. The plasmid of claim 19, wherein the g3p gene of the M13 phage genome is functionally inactivated by the introduction of stop codons within the g3p gene at codons 20, 25, 28 and 30.

24. The plasmid of claim 19, wherein the M13 phage genome is an M13mp19 phage genome.

25. The plasmid according to claim 19, further comprising an antibiotic resistance gene.

* * * * *

```
                              SEQUENCE LISTING

<160> NUMBER OF SEQ ID NOS: 15

<210> SEQ ID NO 1
<211> LENGTH: 35
<212> TYPE: DNA
<213> ORGANISM: Artificial Sequence
<220> FEATURE:
<223> OTHER INFORMATION: synthetic amplification primer

<400> SEQUENCE: 1
ttgatgacgc gtcctattgg ttaaaaaatg agctg                              35

<210> SEQ ID NO 2
<211> LENGTH: 30
<212> TYPE: DNA
<213> ORGANISM: Artificial Sequence
<220> FEATURE:
<223> OTHER INFORMATION: synthetic amplification primer

<400> SEQUENCE: 2
ttgatgacgc gtccgaaatc ggcaaaatcc                                    30

<210> SEQ ID NO 3
<211> LENGTH: 42
<212> TYPE: DNA
<213> ORGANISM: Artificial Sequence
<220> FEATURE:
<223> OTHER INFORMATION: synthetic amplification primer

<400> SEQUENCE: 3
ccacacctgc agcgcttaat gcgccgctac agggcgcgta ct                      42

<210> SEQ ID NO 4
<211> LENGTH: 41
<212> TYPE: DNA
```

```
<213> ORGANISM: Artificial Sequence
<220> FEATURE:
<223> OTHER INFORMATION: synthetic amplification primer

<400> SEQUENCE: 4
tgatttctgc agacgcgtgt ccgaatttct gccattcatc c                    41

<210> SEQ ID NO 5
<211> LENGTH: 30
<212> TYPE: DNA
<213> ORGANISM: Artificial Sequence
<220> FEATURE:
<223> OTHER INFORMATION: synthetic amplification primer

<400> SEQUENCE: 5
taacgctgca gagaacatgg cttcatgtgg                                 30

<210> SEQ ID NO 6
<211> LENGTH: 32
<212> TYPE: DNA
<213> ORGANISM: Artificial Sequence
<220> FEATURE:
<223> OTHER INFORMATION: synthetic amplification primer

<400> SEQUENCE: 6
actgttctgc agagcagaca gttttattgt tc                              32

<210> SEQ ID NO 7
<211> LENGTH: 34
<212> TYPE: DNA
<213> ORGANISM: Artificial Sequence
<220> FEATURE:
<223> OTHER INFORMATION: synthetic amplification primer

<400> SEQUENCE: 7
acaactttcg gatccttcag cggagtgaga atag                            34

<210> SEQ ID NO 8
<211> LENGTH: 36
<212> TYPE: DNA
<213> ORGANISM: Artificial Sequence
<220> FEATURE:
<223> OTHER INFORMATION: synthetic amplification primer

<400> SEQUENCE: 8
ggtggctctg gatccggtga ttttgattat gaaaag                          36

<210> SEQ ID NO 9
<211> LENGTH: 43
<212> TYPE: DNA
<213> ORGANISM: Artificial Sequence
<220> FEATURE:
<223> OTHER INFORMATION: synthetic amplification primer

<400> SEQUENCE: 9
ccatatgaat tctctattga ttgtgacaaa ataaacttat tcc                  43

<210> SEQ ID NO 10
<211> LENGTH: 42
<212> TYPE: DNA
<213> ORGANISM: Artificial Sequence
<220> FEATURE:
<223> OTHER INFORMATION: synthetic amplification primer

<400> SEQUENCE: 10
gaaaggaaca actaaaggaa ttccgaataa taatttttc ac                    42
```

```
<210> SEQ ID NO 11
<211> LENGTH: 48
<212> TYPE: DNA
<213> ORGANISM: Artificial Sequence
<220> FEATURE:
<223> OTHER INFORMATION: synthetic amplification primer

<400> SEQUENCE: 11
gaaagttgat cagcataacc ccatacatga aattcattta ctaacgtc            48

<210> SEQ ID NO 12
<211> LENGTH: 43
<212> TYPE: DNA
<213> ORGANISM: Artificial Sequence
<220> FEATURE:
<223> OTHER INFORMATION: synthetic amplification primer

<400> SEQUENCE: 12
ttttgctgat caactttcaa cagttcaagc ggagtgagaa tag                 43

<210> SEQ ID NO 13
<211> LENGTH: 7889
<212> TYPE: DNA
<213> ORGANISM: Artificial Sequence
<220> FEATURE:
<223> OTHER INFORMATION: synthetic plasmid M13cp

<400> SEQUENCE: 13 gtatttttacc cgtttaatgg aaacttcctc atgaaaaagt ctttagtcct caaagcctct      60
gtagccgttg ctaccctcgt tccgatgctg tctttcgctg ctgagggtga cgatcccgca      120
aaagcggcct ttaactcccct gcaagcctca gcgaccgaat atatcggtta tgcgtgggcg     180
atggttgttg tcattgtcgg cgcaactatc ggtatcaagc tgtttaagaa attcacctcg     240
aaagcaagct gataaaccga tacaattaaa ggctcctttt ggagcctttt ttttggaga      300 ttttcaacgt gaaaaaatta ttattcgcaa ttcctttagt tgttcctttc tattctcact     360
ccgctgaaac tgttgaaagt tgtttagcaa aaccccatac agaaaattca tttactaacg     420
tctggaaaga cgacaaaact ttagatcgtt acgctaacta tgagggttgt ctgtggaatg     480
ctacaggcgt tgtagtttgt actggtgacg aaactcagtg ttacggtaca tgggttccta     540
ttgggcttgc tatccctgaa atgagggtg gtggctctga gggtggcggt tctgagggtg     600
gcggttctga gggtggcggt actaaacctc ctgagtacgg tgatacacct attccgggct     660
atacttatat caaccctctc gacggcactt atccgcctgg tactgagcaa aaccccgcta     720
atcctaatcc ttctcttgag gagtctcagc ctcttaatac tttcatgttt cagaataata     780
ggttccgaaa taggcagggg gcattaactg tttatacggg cactgttact caaggcactg     840
accccgttaa aacttattac cagtacactc ctgtatcatc aaaagccatg tatgacgctt     900
actggaacgg taaattcaga gactgcgctt tccattctgg ctttaatgaa gatccattcg     960
tttgtgaata tcaaggccaa tcgtctgacc tgcctcaacc tcctgtcaat gctggcggcg    1020
gctctggtgg tggttctggt ggcggctctg agggtggtgg ctctgagggt ggcggttctg    1080
agggtggcgg ctctgaggga ggcggttccg gtggtggctc tggttccggt gattttgatt    1140
atgaaaagat ggcaaacgct aatagggggc tatgaccga aatgccgat gaaaacgcgc     1200 tacagtctga cgctaaaggc aaacttgatt ctgtcgctac tgattacggt gctgctatcg    1260
atggtttcat tggtgacgtt tccggccttg ctaatggtaa tggtgctact ggtgattttg    1320
ctggctctaa ttcccaaatg gctcaagtcg gtgacggtga taattcacct ttaatgaata    1380
```

```
atttccgtca atatttacct tccctccctc aatcggttga atgtcgccct tttgtcttta    1440
gcgctggtaa accatatgaa ttttctattg attgtgacaa aataaactta ttccgtggtg    1500
tctttgcgtt tcttttatat gttgccacct ttatgtatgt attttctacg tttgctaaca    1560
tactgcgtaa taaggagtct taatcatgcc agttcttttg ggtattccgt tattattgcg    1620
tttcctcggt ttccttctgg taactttgtt cggctatctg cttacttttc ttaaaaaggg    1680
cttcggtaag atagctattg ctatttcatt gtttcttgct cttattattg gcttaactc     1740
aattcttgtg ggttatctct ctgatattag cgctcaatta ccctctgact ttgttcaggg    1800
tgttcagtta attctcccgt ctaatgcgct tccctgtttt tatgttattc tctctgtaaa    1860
ggctgctatt ttcatttttg acgttaaaca aaaaatcgtt tcttatttgg attgggataa    1920
ataatatggc tgtttatttt gtaactggca aattaggctc tggaaagacg ctcgttagcg    1980
ttggtaagat tcaggataaa attgtagctg ggtgcaaaat agcaactaat cttgatttaa    2040
ggcttcaaaa cctcccgcaa gtcgggaggt tcgctaaaac gcctcgcgtt cttagaatac    2100
cggataagcc ttctatatct gatttgcttg ctattgggcg cggtaatgat tcctacgatg    2160
aaaataaaaa cggcttgctt gttctcgatg agtgcggtac ttggtttaat acccgttctt    2220
ggaatgataa ggaaagacag ccgattattg attggtttct acatgctcgt aaattaggat    2280
gggatattat ttttcttgtt caggacttat ctattgttga taaacaggcg cgttctgcat    2340
tagctgaaca tgttgtttat tgtcgtcgtc tggacagaat tactttacct tttgtcggta    2400
ctttatattc tcttattact ggctcgaaaa tgcctctgcc taaattacat gttggcgttg    2460
ttaaatatgg cgattctcaa ttaagcccta ctgttgagcg ttggctttat actggtaaga    2520
atttgtataa cgcatatgat actaaacagg ctttttctag taattatgat tccggtgttt    2580
attcttattt aacgccttat ttatcacacg gtcggtattt caaaccatta aatttaggtc    2640
agaagatgaa attaactaaa atatatttga aaaagttttc tcgcgttctt tgtcttgcga    2700
ttggatttgc atcagcattt acatatagtt atataaccca acctaagccg gaggttaaaa    2760
aggtagtctc tcagacctat gattttgata aattcactat tgactcttct cagcgtctta    2820
atctaagcta tcgctatgtt ttcaaggatt ctaagggaaa attaattaat agcgacgatt    2880
tacagaagca aggttattca ctcacatata ttgatttatg tactgttttcc attaaaaaag   2940
gtaattcaaa tgaaattgtt aaatgtaatt aattttgttt tcttgatgtt tgtttcatca    3000
tcttcttttg ctcaggtaat tgaaatgaat aattcgcctc tgcgcgattt tgtaacttgg    3060
tattcaaagc aatcaggcga atccgttatt gtttctcccg atgtaaaagg tactgttact    3120
gtatattcat ctgacgttaa acctgaaaat ctacgcaatt tctttatttc tgttttacgt    3180
gctaataatt ttgatatggt tggttcaatt ccttccataa ttcagaagta taatccaaac    3240
aatcaggatt atattgatga attgccatca tctgataatc aggaatatga tgataattcc    3300
gctccttctg gtggtttctt tgttccgcaa aatgataatg ttactcaaac ttttaaaatt    3360
aataacgttc gggcaaagga tttaatacga gttgtcgaat gtttgtaaa gtctaatact    3420
tctaaatcct caaatgtatt atctattgac ggctctaatc tattagttgt tagtgcacct    3480
aaagatattt tagataacct tcctcaattc ctttctactg ttgatttgcc aactgaccag    3540
atattgattg agggtttgat atttgaggtt cagcaaggtg atgctttaga ttttcattt     3600
gctgctggct ctcagcgtgg cactgttgca ggcggtgtta atactgaccg cctcacctct    3660
gttttatctt ctgctggtgg ttcgttcggt attttaatg gcgatgtttt agggctatca    3720
gttcgcgcat taaagactaa tagccattca aaaatattgt ctgtgccacg tattcttacg    3780
```

```
ctttcaggtc agaagggttc tatctctgtt ggccagaatg tccctttat tactggtcgt      3840 gtgactggtg aatctgccaa tgtaaataat ccatttcaga cgattgagcg tcaaaatgta      3900
ggtatttcca tgagcgtttt tcctgttgca atggctggcg gtaatattgt tctggatatt      3960
accagcaagg ccgatagttt gagttcttct actcaggcaa gtgatgttat tactaatcaa      4020
agaagtattg ctacaacggt taatttgcgt gatggacaga ctcttttact cggtggcctc      4080
actgattata aaaacacttc tcaagattct ggcgtaccgt tcctgtctaa aatccctta      4140 atcggcctcc tgtttagctc ccgctctgat tccaacgagg aaagcacgtt atacgtgctc      4200
gtcaaagcaa ccatagtacg cgccctgtag cggcgcatta gcgcctgca gagaacatgg      4260 cttcatgtgg caggagaaaa aaggctgcac cggtgcgtca gcagaatatg tgatacagga      4320
tatattccgc ttcctcgctc actgactcgc tacgctcggt cgttcgactg cggcgagcgg      4380
aaatggctta cgaacggggc ggagatttcc tggaagatgc caggaagata cttaacaggg      4440
aagtgagagg gccgcggcaa agccgttttt ccataggctc cgcccccctg acaagcatca      4500
cgaaatctga cgctcaaatc agtggtggcg aaacccgaca ggactataaa gataccaggc      4560
gtttccccct ggcggctccc tcgtgcgctc tcctgttcct gcctttcggt ttaccggtgt      4620
cattccgctg ttatggccgc gtttgtctca ttccacgcct gacactcagt tccgggtagg      4680
cagttcgctc caagctggac tgtatgcacg aacccccgt tcagtccgac cgctgcgcct      4740
tatccggtaa ctatcgtctt gagtccaacc cggaaagaca tgcaaaagca ccactggcag      4800
cagccactgg taattgattt agaggagtta gtcttgaagt catgcgccgg ttaaggctaa      4860
actgaaagga caagttttgg tgactgcgct cctccaagcc agttacctcg gttcaaagag      4920
ttggtagctc agagaacctt cgaaaaaccg ccctgcaagg cggtttttc gttttcagag      4980 caagagatta cgcgcagacc aaaacgatct caagaagatc atcttattaa ggggtctgac      5040
gctcagtgga acgaaaactc acgttaaggg attttggtca tgaacaataa aactgtctgc      5100
tctgcaggac gcgtgtccga atttctgcca ttcatccgct tattatcact tattcaggcg      5160
tagcaccagg cgtttaaggg caccaataac tgccttaaaa aaattacgcc ccgccctgcc      5220
actcatcgca gtactgttgt aattcattaa gcattctgcc gacatggaag ccatcacaaa      5280
cggcatgatg aacctgaatc gccagcggca tcagcacctt gtcgccttgc gtataatatt      5340
tgcccatggt gaaaacgggg gcgaagaagt tgtccatatt ggccacgttt aaatcaaaac      5400
tggtgaaact cacccaggga ttggctgaga cgaaaaacat attctcaata aaccctttag      5460
ggaaatagcc caggttttca ccgtaacacg ccacatcttg cgaatatatg tgtagaaact      5520
gccggaaatc gtcgtggtat tcactccaga gcgatgaaaa cgtttcagtt tgctcatgga      5580
aaacggtgta acaagggtga acactatccc atatcaccag ctcaccgtct ttcattgcca      5640
tacgaaattc cggatgagca ttcatcaggc gggcaagaat gtgaataaag gccggataaa      5700
acttgtgctt atttttcttt acggtctttta aaaaggccgt aatatccagc tgaacggtct      5760
ggttataggt acattgagca actgactgaa atgcctcaaa atgttcttta cgatgccatt      5820
gggatatatc aacggtggta tatccagtga ttttttctc catttagct tccttagctc      5880 ctgaaaatct cgataactca aaaaatacgc ccggtagtga tcttatttca ttatggtgaa      5940
agttggaacc tcttacgtgc cgatcaacgt ctcattttcg ccaaaagttg gcccagggct      6000
tcccggtatc aacagggaca ccaggattta tttattctgc gaagtgatct tccgtcacag      6060
gtatttattc ggcacacgcg tcctattggtt aaaaaatgag ctgatttaac aaaaatttaa      6120
cgcgaatttt aacaaaatat taacgtttac aatttaaata tttgcttata caatcttcct      6180
```

```
gtttttgggg cttttctgat tatcaaccgg ggtacatatg attgacatgc tagttttacg    6240
attaccgttc atcgattctc ttgtttgctc cagactctca ggcaatgacc tgatagcctt    6300
tgtagatctc tcaaaaatag ctaccctctc cggcatgaat ttatcagcta gaacggttga    6360
atatcatatt gatggtgatt tgactgtctc cggccttcct cacccttttg aatctttacc    6420
tacacattac tcaggcattg catttaaaat atatgagggt tctaaaaatt tttatccttg    6480
cgttgaaata aaggcttctc ccgcaaaagt attacagggt cataatgttt ttggtacaac    6540
cgatttagct ttatgctctg aggctttatt gcttaatttt gctaattctt tgccttgcct    6600
gtatgattta ttggatgtta atgctactac tattagtaga attgatgcca ccttttcagc    6660
tcgcgcccca aatgaaaata tagctaaaca ggttattgac catttgcgaa atgtatctaa    6720
tggtcaaact aaatctactc gttcgcagaa ttgggaatca actgttacat ggaatgaaac    6780
ttccagacac cgtactttag ttgcatattt aaaacatgtt gagctacagc accagattca    6840
gcaattaagc tctaagccat ccgcaaaaat gacctcttat caaaaggagc aattaaaggt    6900
actctctaat cctgacctgt tggagtttgc ttccggtctg gttcgctttg aagctcgaat    6960
taaaacgcga tatttgaagt cttttcgggct tcctcttaat cttttttgatg caatccgctt    7020 tgcttctgac tataatagtc agggtaaaga cctgattttt gatttatggt cattctcgtt    7080
ttctgaactg tttaaagcat tgagggggga ttcaatgaat attttgatgacg attccgcagt    7140 attggacgct atccagtcta aacattttac tattacccccc tctggcaaaa cttcttttgc    7200
aaaagcctct cgctattttg gttttttatcg tcgtctggta acgagggt atgatagtgt    7260 tgctcttact atgcctcgta attccttttg gcgttatgta tctgcattag ttgaatgtgg    7320
tattcctaaa tctcaactga tgaatctttc tacctgtaat aatgttgttc cgttagttcg    7380
ttttattaac gtagattttt cttcccaacg tcctgactgg tataatgagc cagttcttaa    7440
aatcgcataa ggtaattcac aatgattaaa gttgaaatta aaccatctca agcccaattt    7500
actactcgtt ctggtgtttc tcgtcagggc aagccttatt cactgaatga gcagctttgt    7560
tacgttgatt tgggtaatga atatccggtt cttgtcaaga ttactcttga tgaaggtcag    7620
ccagcctatg cgcctggtct gtacaccgtt catctgtcct ctttcaaagt tggtcagttc    7680 ggttcccta tgattgaccg tctgcgcctc gttccggcta agtaacatgg agcaggtcgc    7740
ggatttcgac acaatttatc aggcgatgat acaaatctcc gttgtacttt gtttcgcgct    7800
tggtataatc gctggggtc aaagatgagt gttttagtgt attctttcgc ctctttcgtt    7860
ttaggttggt gccttcgtag tggcattac                                     7889

<210> SEQ ID NO 14
<211> LENGTH: 7136
<212> TYPE: DNA
<213> ORGANISM: Artificial Sequence
<220> FEATURE:
<223> OTHER INFORMATION: synthetic plasmid M13cp-CT

<400> SEQUENCE: 14
atttgctgct ggctctcagc gtggcactgt tgcaggcggt gttaatactg accgcctcac      60 ctctgttta tcttctgctg gtggttcgtt cggtattttt aatggcgatg ttttagggct     120
atcagttcgc gcattaaaga ctaatagcca ttcaaaaata ttgtctgtgc cacgtattct     180
tacgctttca ggtcagaagg gttctatctc tgttggccag aatgtcccctt ttattactgg     240 tcgtgtgact ggtgaatctg ccaatgtaaa taatccattt cagacgattg agcgtcaaaa     300
tgtaggtatt tccatgagcg ttttcctgt tgcaatggct ggcggtaata ttgttctgga     360
```

```
tattaccagc aaggccgata gttttgagttc ttctactcag gcaagtgatg ttattactaa    420
tcaaagaagt attgctacaa cggttaattt gcgtgatgga cagactcttt tactcggtgg    480
cctcactgat tataaaaaca cttctcaaga ttctggcgta ccgttcctgt ctaaaatccc    540
tttaatcggc ctcctgttta gctcccgctc tgattccaac gaggaaagca cgttatacgt    600
gctcgtcaaa gcaaccatag tacgcgccct gtagcggcgc attaagcgcc tgcagagaac    660
atggcttcat gtggcaggag aaaaaaggct gcaccggtgc gtcagcagaa tatgtgatac    720
aggatatatt ccgcttcctc gctcactgac tcgctacgct cggtcgttcg actgcggcga    780
gcggaaatgg cttacgaacg gggcggagat tcctggaagat gccaggaa gatacttaac     840
agggaagtga gagggccgcg gcaaagccgt ttttccatag gctccgcccc cctgacaagc    900
atcacgaaat ctgacgctca atcagtggtg gcgaaaccc gacaggacta taagatacc      960
aggcgtttcc ccctggcggc tccctcgtgc gctctcctgt tcctgccttt cggtttaccg   1020
gtgtcattcc gctgttatgg ccgcgtttgt ctcattccac gcctgacact cagttccggg   1080
taggcagttc gctccaagct ggactgtatg cacgaacccc ccgttcagtc cgaccgctgc   1140
gccttatccg gtaactatcg tcttgagtcc aacccggaaa gacatgcaaa agcaccactg   1200
gcagcagcca ctggtaattg atttagagga gttagtcttg aagtcatgcg ccggttaagg   1260
ctaaactgaa aggacaagtt tggtgactg cgctcctcca agccagttac ctcggttcaa    1320
agagttggta gctcagagaa ccttcgaaaa accgccctgc aaggcggttt tttcgttttc   1380
agagcaagag attacgcgca gaccaaaacg atctcaagaa gatcatctta ttaaggggtc   1440
tgacgctcag tggaacgaaa actcacgtta agggattttg gtcatgaaca ataaaactgt   1500
ctgctctgca ggacgcgtgt ccgaatttct gccattcatc cgcttattat cacttattca   1560
ggcgtagcac caggcgttta agggcaccaa taactgcctt aaaaaaatta cgccccgccc   1620
tgccactcat cgcagtactg ttgtaattca ttaagcattc tgccgacatg gaagccatca   1680
caaacggcat gatgaacctg aatcgccagc ggcatcagca ccttgtcgcc ttgcgtataa   1740
tatttgccca tggtgaaaac gggggcgaag aagttgtcca tattggccac gtttaaatca   1800
aaactggtga aactcaccca gggattggct gagacgaaaa acatattctc aataaaccct   1860
ttagggaaat aggccaggtt ttcaccgtaa cacgccacat cttgcgaata tatgtgtaga   1920
aactgccgga aatcgtcgtg gtattcactc cagagcgatg aaaacgtttc agtttgctca   1980
tggaaaacgg tgtaacaagg gtgaacacta tcccatatca ccagctcacc gtctttcatt   2040
gccatacgaa attccggatg agcattcatc aggcgggcaa gaatgtgaat aaaggccgga   2100
taaaacttgt gcttattttt ctttacggtc tttaaaaagg ccgtaatatc cagctgaacg   2160
gtctggttat aggtacattg agcaactgac tgaaatgcct caaaatgttc tttacgatgc   2220
cattgggata tatcaacggt ggtatatcca gtgatttttt tctccatttt agcttcctta   2280
gctcctgaaa atctcgataa ctcaaaaaat acgcccggta gtgatcttat ttcattatgg   2340
tgaaagttgg aacctcttac gtgccgatca acgtctcatt ttcgccaaaa gttggcccag   2400
ggcttcccgg tatcaacagg gacaccagga tttatttatt ctgcgaagtg atcttccgtc   2460
acaggtattt attcggacac gcgtcctatt ggttaaaaaa tgagctgatt taacaaaaat   2520
ttaacgcgaa ttttaacaaa atattaacgt ttacaattta aatatttgct tatacaatct   2580
tcctgttttt ggggctttc tgattatcaa ccggggtaca tatgattgac atgctagttt   2640
tacgattacc gttcatcgat tctccttgttt gctccagact ctcaggcaat gacctgatag   2700
cctttgtaga tctctcaaaa atagctaccc tctccggcat gaatttatca gctagaacgg   2760
```

```
ttgaatatca tatttgatggt gatttgactg tctccggcct ttctcaccct tttgaatctt    2820
tacctacaca ttactcaggc attgcattta aaatatatga gggttctaaa aatttttatc    2880
cttgcgttga aataaaggct tctcccgcaa aagtattaca gggtcataat gttttttggta   2940
caaccgattt agctttatgc tctgaggctt tattgcttaa ttttgctaat tctttgcctt    3000
gcctgtatga tttattggat gttaatgcta ctactattag tagaattgat gccaccttt    3060
cagctcgcgc cccaaatgaa aatatagcta acaggttat tgaccatttg cgaaatgtat    3120
ctaatggtca aactaaatct actcgttcgc agaattggga atcaactgtt acatggaatg   3180
aaacttccag acaccgtact ttagttgcat atttaaaaca tgttgagcta cagcaccaga   3240
ttcagcaatt aagctctaag ccatccgcaa aaatgacctc ttatcaaaag gagcaattaa   3300
aggtactctc taatcctgac ctgttggagt ttgcttccgg tctggttcgc tttgaagctc   3360
gaattaaaac gcgatatttg aagtctttcg gcttcctct taatctttt gatgcaatcc    3420
gctttgcttc tgactataat agtcagggta aagacctgat ttttgattta tggtcattct   3480
cgttttctga actgtttaaa gcatttgagg gggattcaat gaatatttat gacgattccg   3540
cagtattgga cgctatccag tctaaacatt ttactattac cccctctggc aaaacttctt   3600
ttgcaaaagc ctctcgctat tttggttttt atcgtcgtct ggtaaacgag ggttatgata   3660
gtgttgctct tactatgcct cgtaattcct tttggcgtta tgtatctgca ttagttgaat   3720
gtggtattcc taaatctcaa ctgatgaatc tttctacctg taataatgtt gttccgttag   3780
ttcgttttat taacgtagat ttttcttccc aacgtcctga ctggtataat gagccagttc   3840
ttaaaatcgc ataaggtaat tcacaatgat taaagttgaa attaaaccat ctcaagccca   3900
atttactact cgttctggtg tttctcgtca gggcaagcct tattcactga atgagcagct   3960
ttgttacgtt gatttgggta atgaatatcc ggttcttgtc aagattactc ttgatgaagg   4020
tcagccagcc tatgcgcctg gtctgtacac cgttcatctg tcctctttca aagttggtca   4080
gttcggttcc cttatgattg accgtctgcg cctcgttccg gctaagtaac atggagcagg   4140
tcgcggattt cgacacaatt tatcaggcga tgatacaaat ctccgttgta ctttgtttcg   4200
cgcttggtat aatcgctggg ggtcaaagat gagtgtttta gtgtattctt tcgcctcttt   4260
cgttttaggt tggtgccttc gtagtggcat tacgtatttt acccgtttaa tggaaacttc   4320
ctcatgaaaa agtctttagt cctcaaagcc tctgtagccg ttgctaccct cgttccgatg   4380
ctgtctttcg ctgctgaggg tgacgatccc gcaaaagcgg cctttaactc cctgcaagcc   4440
tcagcgaccg aatatatcgg ttatgcgtgg gcgatggttg ttgtcattgt cggcgcaact   4500
atcggtatca agctgtttaa gaaattcacc tcgaaagcaa gctgataaac cgatacaatt   4560
aaaggctcct tttggagcct tttttttgg agatttcaa cgtgaaaaaa ttattattcg    4620
caattccttt agttgttcct ttctattctc actccgctga aggatccggt gattttgatt   4680
atgaaaagat ggcaaacgct aataagggg ctatgaccga aaatgccgat gaaaacgcgc    4740
tacagtctga cgctaaaggc aaacttgatt ctgtcgctac tgattacggt gctgctatcg   4800
atggtttcat tggtgacgtt tccggccttg ctaatggtaa tggtgctact ggtgattttg   4860
ctggctctaa ttcccaaatg gctcaagtcg gtgacggtga taattcacct ttaatgaata   4920
atttccgtca atatttacct tccctccctc aatcggttga atgtcgccct tttgtctta    4980
gcgctggtaa accatatgaa ttttctattg attgtgacaa aataaactta ttccgtggtg   5040
tctttgcgtt ctcttttatat gttgccacct ttatgtatgt attttctacg tttgctaaca   5100
tactgcgtaa taaggagtct taatcatgcc agttcttttg ggtattccgt tattattgcg   5160
```

```
tttcctcggt tcccttctgg taactttgtt cggctatctg cttactttc ttaaaaaggg    5220
cttcggtaag atagctattg ctatttcatt gtttcttgct cttattattg ggcttaactc    5280
aattcttgtg ggttatctct ctgatattag cgctcaatta ccctctgact ttgttcaggg    5340
tgttcagtta attctcccgt ctaatgcgct tccctgtttt tatgttattc tctctgtaaa    5400
ggctgctatt tcattttttg acgttaaaca aaaaatcgtt tcttatttgg attgggataa    5460
ataatatggc tgtttatttt gtaactggca aattaggctc tggaaagacg ctcgttagcg    5520
ttggtaagat tcaggataaa attgtagctg ggtgcaaaat agcaactaat cttgatttaa    5580
ggcttcaaaa cctcccgcaa gtcgggaggt tcgctaaaac gcctcgcgtt cttagaatac    5640
cggataagcc ttctatatct gatttgcttg ctattgggcg cggtaatgat tcctacgatg    5700
aaaataaaaa cggcttgctt gttctcgatg agtgcggtac ttggtttaat acccgttctt    5760
ggaatgataa ggaaagacag ccgattattg attggtttct acatgctcgt aaattaggat    5820
gggatattat ttttcttgtt caggacttat ctattgttga taaacaggcg cgttctgcat    5880
tagctgaaca tgttgtttat tgtcgtcgtc tggacagaat tactttacct tttgtcggta    5940
ctttatattc tcttattact ggctcgaaaa tgcctctgcc taaattacat gttggcgttg    6000
ttaaatatgg cgattctcaa ttaagcccta ctgttgagcg ttggctttat actggtaaga    6060
atttgtataa cgcatatgat actaaacagg cttttttctag taattatgat tccggtgttt    6120
attcttattt aacgccttat ttatcacacg gtcggtattt caaaccatta aatttaggtc    6180
agaagatgaa attaactaaa atatatttga aaaagttttc tcgcgttctt tgtcttgcga    6240
ttggatttgc atcagcattt acatatagtt atataaccca acctaagccg gaggttaaaa    6300
aggtagtctc tcagacctat gattttgata aattcactat tgactcttct cagcgtctta    6360
atctaagcta tcgctatgtt ttcaaggatt ctaagggaaa attaattaat agcgacgatt    6420
tacagaagca aggttattca ctcacatata ttgatttatg tactgttttcc attaaaaaag    6480
gtaattcaaa tgaaattgtt aaatgtaatt aattttgttt tcttgatgtt tgtttcatca    6540
tcttcttttg ctcaggtaat tgaaatgaat aattcgcctc tgcgcgattt tgtaacttgg    6600
tattcaaagc aatcaggcga atccgttatt gtttctcccg atgtaaaagg tactgttact    6660
gtatattcat ctgacgttaa acctgaaaat ctacgcaatt tctttatttc tgttttacgt    6720
gctaataatt tgatatggt tggttcaatt ccttccataa ttcagaagta taatccaaac    6780
aatcaggatt atattgatga attgccatca tctgataatc aggaatatga tgataattcc    6840
gctccttctg gtggtttctt tgttccgcaa aatgataatg ttactcaaac ttttaaaatt    6900
aataacgttc gggcaaagga tttaatacga gttgtcgaat tgtttgtaaa gtctaatact    6960
tctaaatcct caaatgtatt atctattgac ggctctaatc tattagttgt tagtgcacct    7020
aaagatattt tagataacct tcctcaattc ctttctactg ttgatttgcc aactgaccag    7080
atattgattg agggtttgat atttgaggtt cagcaaggtg atgctttaga tttttc         7136
```

<210> SEQ ID NO 15
<211> LENGTH: 6759
<212> TYPE: DNA
<213> ORGANISM: Artificial Sequence
<220> FEATURE:
<223> OTHER INFORMATION: synthetic plasmid M13cp-dg3

<400> SEQUENCE: 15

```
gtacaccgtt catctgtcct ctttcaaagt tggtcagttc ggttccctta tgattgaccg      60
tctgcgcctc gttccggcta agtaacatgg agcaggtcgc ggatttcgac acaatttatc     120
```

-continued

```
aggcgatgat acaaatctcc gttgtacttt gtttcgcgct tggtataatc gctggggtc      180 aaagatgagt gttttagtgt attctttcgc ctctttcgtt ttaggttggt gccttcgtag     240
tggcattacg tattttaccc gtttaatgga aacttcctca tgaaaaagtc tttagtcctc     300
aaagcctctg tagccgttgc taccctcgtt ccgatgctgt ctttcgctgc tgagggtgac     360
gatcccgcaa aagcggcctt taactccctg caagcctcag cgaccgaata tatcggttat    420
gcgtgggcga tggttgttgt cattgtcggc gcaactatcg gtatcaagct gtttaagaaa    480
ttcacctcga aagcaagctg ataaaccgat acaattaaag gctccttttg gagcctttttt  540 ttttggagat tttcaacgtg aaaaaattat tattcggaat tctctattga ttgtgacaaa    600
ataaacttat tccgtggtgt ctttgcgttt cttttatatg ttgccacctt tatgtatgta    660
ttttctacgt ttgctaacat actgcgtaat aaggagtctt aatcatgcca gttcttttgg    720
gtattccgtt attattgcgt ttcctcggtt tccttctggt aactttgttc ggctatctgc    780
ttacttttct taaaagggc ttcggtaaga tagctattgc tatttcattg tttcttgctc     840
ttattattgg gcttaactca attcttgtgg gttatctctc tgatattagc gctcaattac    900
cctctgactt tgttcagggt gttcagttaa ttctcccgtc taatgcgctt ccctgttttt    960
atgttattct ctctgtaaag gctgctattt tcattttga cgttaaacaa aaaatcgttt    1020
cttatttgga ttgggataaa taatatggct gtttatttg taactggcaa attaggctct    1080
ggaaagacgc tcgttagcgt tggtaagatt caggataaaa ttgtagctgg gtgcaaaata    1140
gcaactaatc ttgatttaag gcttcaaaac ctcccgcaag tcgggaggtt cgctaaaacg    1200
cctcgcgttc ttagaatacc ggataagcct tctatatctg atttgcttgc tattgggcgc    1260
ggtaatgatt cctacgatga aaataaaaac ggcttgcttg ttctcgatga gtgcggtact    1320
tggtttaata cccgttcttg gaatgataag gaaagacagc cgattattga ttggtttcta    1380
catgctcgta aattaggatg ggatattatt tttcttgttc aggacttatc tattgttgat    1440
aaacaggcgc gttctgcatt agctgaacat gttgtttatt gtcgtcgtct ggacagaatt    1500
actttacctt ttgtcggtac tttatattct cttattactg gctcgaaaat gcctctgcct    1560
aaattacatg ttggcgttgt taaatatggc gattctcaat taagccctac tgttgagcgt    1620
tggctttata ctggtaagaa tttgtataac gcatatgata ctaaacaggc ttttctagt    1680 aattatgatt ccggtgttta ttcttattta acgccttatt tatcacacgg tcggtatttc    1740
aaaccattaa atttaggtca gaagatgaaa ttaactaaaa tatatttgaa aaagttttct    1800
cgcgttcttt gtcttgcgat tggatttgca tcagcattta catatagtta tataacccaa    1860
cctaagccgg aggttaaaaa ggtagtctct cagacctatg attttgataa attcactatt    1920
gactcttctc agcgtcttaa tctaagctat cgctatgttt tcaaggattc taagggaaaa    1980
ttaattaata gcgacgattt acagaagcaa ggttattcac tcacatatat tgatttatgt    2040
actgtttcca ttaaaaaagg taattcaaat gaaattgtta aatgtaatta attttgtttt    2100
cttgatgttt gtttcatcat cttctttttgc tcaggtaatt gaaatgaata attcgcctct    2160
gcgcgatttt gtaacttggt attcaaagca atcaggcgaa tccgttattg tttctcccga    2220
tgtaaaaggt actgttactg tatattcatc tgacgttaaa cctgaaaatc tacgcaattt    2280
ctttatttct gttttacgtg ctaataattt tgatatggtt ggttcaattc cttccataat    2340
tcagaagtat aatccaaaca atcaggatta tattgatgaa ttgccatcat ctgataatca    2400
ggaatatgat gataattccg ctccttctgg tggtttcttt gttccgcaaa atgataatgt    2460
tactcaaact tttaaaatta ataacgttcg ggcaaaggat ttaatacgag ttgtcgaatt    2520
```

```
gtttgtaaag tctaatactt ctaaatcctc aaatgtatta tctattgacg gctctaatct  2580
attagttgtt agtgcaccta aagatatttt agataaccct cctcaattcc tttctactgt  2640
tgatttgcca actgaccaga tattgattga gggtttgata tttgaggttc agcaaggtga  2700
tgctttagat ttttcatttg ctgctggctc tcagcgtggc actgttgcag gcggtgttaa  2760
tactgaccgc ctcacctctg ttttatcttc tgctggtggt tcgttcggta ttttaatgg   2820 cgatgtttta gggctatcag ttcgcgcatt aaagactaat agccattcaa aatattgtc   2880 tgtgccacgt attcttacgc tttcaggtca aagggttct atctctgttg ccagaatgt    2940 cccttttatt actggtcgtg tgactggtga atctgccaat gtaaataatc catttcagac  3000
gattgagcgt caaaatgtag gtatttccat gagcgttttt cctgttgcaa tggctggcgg  3060
taatattgtt ctggatatta ccagcaaggc cgatagtttg agttcttcta ctcaggcaag  3120
tgatgttatt actaatcaaa gaagtattgc tacaacggtt aatttgcgtg atggacagac  3180
tcttttactc ggtggcctca ctgattataa aaacacttct caagattctg gcgtaccgtt  3240
cctgtctaaa atccctttaa tcggcctcct gtttagctcc cgctctgatt ccaacgagga  3300
aagcacgtta tacgtgctcg tcaaagcaac catagtacgc gccctgtagc ggcgcattaa  3360
gcgcctgcag agaacatggc ttcatgtggc aggagaaaaa aggctgcacc ggtgcgtcag  3420
cagaatatgt gatacaggat atattccgct tcctcgctca ctgactcgct acgctcggtc  3480
gttcgactgc ggcgagcgga atggcttac gaacggggcg gagatttcct ggaagatgcc    3540
aggaagatac ttaacaggga agtgagaggg ccgcggcaaa gccgttttc cataggctcc    3600 gcccccctga caagcatcac gaaatctgac gctcaaatca gtggtggcga aacccgacag  3660
gactataaag ataccaggcg tttccccctg gcggctccct cgtgcgctct cctgttcctg  3720
cctttcggtt taccggtgtc attccgctgt tatggccgcg tttgtctcat tccacgcctg  3780
acactcagtt ccgggtaggc agttcgctcc aagctggact gtatgcacga acccccccgtt 3840 cagtccgacc gctgcgcctt atccggtaac tatcgtcttg agtccaaccc ggaaagacat  3900
gcaaaagcac cactggcagc agccactggt aattgattta gaggagttag tcttgaagtc  3960
atgcgccggt taaggctaaa ctgaaaggac aagtttggt gactgcgctc ctccaagcca   4020
gttacctcgg ttcaaagagt tggtagctca gagaaccttc gaaaaaccgc cctgcaaggc  4080
ggttttttcg ttttcagagc aagagattac gcgcagacca aaacgatctc aagaagatca  4140
tcttattaag gggtctgacg ctcagtggaa cgaaaactca cgttaaggga ttttggtcat  4200
gaacaataaa actgtctgct ctgcaggacg cgtgtccgaa tttctgccat tcatccgctt  4260
attatcactt attcaggcgt agcaccaggc gtttaagggc accaataact gccttaaaaa  4320
aattacgccc cgccctgcca ctcatcgcag tactgttgta attcattaag cattctgccg  4380
acatggaagc catcacaaac ggcatgatga acctgaatcg ccagcggcat cagcaccttg  4440
tcgccttgcg tataatattt gcccatggtg aaaacggggg cgaagaagtt gtccatattg  4500
gccacgttta aatcaaaact ggtgaaactc acccagggat tggctgagac gaaaaacata  4560
ttctcaataa acccttaggg gaataggcc aggttttcac cgtaacacgc cacatcttgc    4620
gaatatatgt gtagaaactg ccggaaatcg tcgtggtatt cactccagag cgatgaaaac  4680
gtttcagttt gctcatggaa aacggtgtaa caagggtgaa cactatccca tatcaccagc  4740
tcaccgtctt tcattgccat acgaaattcc ggatgagcat tcatcaggcg ggcaagaatg  4800
tgaataaagg ccggataaaa cttgtgctta ttttcttta cggtctttaa aaaggccgta   4860
atatccagct gaacggtctg gttataggta cattgagcaa ctgactgaaa tgcctcaaaa  4920
```

```
tgttctttac gatgccattg ggatatatca acggtggtat atccagtgat ttttttctcc      4980
attttagctt ccttagctcc tgaaaatctc gataactcaa aaaatacgcc cggtagtgat      5040
cttatttcat tatggtgaaa gttggaacct cttacgtgcc gatcaacgtc tcattttcgc      5100
caaaagttgg cccagggctt cccggtatca acagggacac caggatttat ttattctgcg      5160
aagtgatctt ccgtcacagg tatttattcg gacacgcgtc ctattggtta aaaaatgagc      5220
tgatttaaca aaaatttaac gcgaatttta acaaaatatt aacgtttaca atttaaatat      5280
ttgcttatac aatcttcctg tttttggggc ttttctgatt atcaaccggg gtacatatga      5340
ttgacatgct agttttacga ttaccgttca tcgattctct tgtttgctcc agactctcag      5400
gcaatgacct gatagccttt gtagatctct caaaaatagc taccctctcc ggcatgaatt      5460
tatcagctag aacggttgaa tatcatattg atggtgattt gactgtctcc ggcctttctc      5520
acccttttga atctttacct acacattact caggcattgc atttaaaata tatgagggtt      5580
ctaaaaattt ttatccttgc gttgaaataa aggcttctcc cgcaaaagta ttacagggtc      5640
ataatgtttt tggtacaacc gatttagctt tatgctctga ggctttattg cttaattttg      5700
ctaattcttt gccttgcctg tatgatttat tggatgttaa tgctactact attagtagaa      5760
ttgatgccac cttttcagct cgcgccccaa atgaaaatat agctaaacag gttattgacc      5820
atttgcgaaa tgtatctaat ggtcaaacta aatctactcg ttcgcagaat tgggaatcaa      5880
ctgttacatg gaatgaaact tccagacacc gtactttagt tgcatattta aaacatgttg      5940
agctacagca ccagattcag caattaagct ctaagccatc cgcaaaaatg acctcttatc      6000
aaaaggagca attaaaggta ctctctaatc ctgacctgtt ggagtttgct tccggtctgg      6060
ttcgctttga agctcgaatt aaaacgcgat atttgaagtc tttcgggctt cctcttaatc      6120
tttttgatgc aatccgcttt gcttctgact ataatagtca gggtaaagac ctgattttg      6180 atttatggtc attctcgttt tctgaactgt ttaaagcatt tgaggggggat tcaatgaata      6240 tttatgacga ttccgcagta ttggacgcta tccagtctaa acattttact attacccccct      6300 ctggcaaaac ttcttttgca aaagcctctc gctatttggg ttttatcgt cgtctggtaa      6360 acgagggtta tgatagtgtt gctcttacta tgcctcgtaa ttccttttgg cgttatgtat      6420
ctgcattagt tgaatgtggt attcctaaat ctcaactgat gaatctttct acctgtaata      6480
atgttgttcc gttagttcgt tttattaacg tagattttc ttcccaacgt cctgactggt      6540
ataatgagcc agttcttaaa atcgcataag gtaattcaca atgattaaag ttgaaattaa      6600
accatctcaa gcccaattta ctactcgttc tggtgtttct cgtcagggca agccttattc      6660
actgaatgag cagctttgtt acgttgattt gggtaatgaa tatccggttc ttgtcaagat      6720
tactcttgat gaaggtcagc cagcctatgc gcctggtct                            6759
```